United States Patent [19]
Lennox et al.

[11] Patent Number: 5,861,296
[45] Date of Patent: Jan. 19, 1999

[54] **PURIFIED THERMOSTABLE INORGANIC PYROPHOSPHATASE OBTAINABLE FROM *THERMOCOCCUS LITORALIS***

[75] Inventors: Tricia Lennox, Philadelphia, Pa.; Barton E. Slatko, Ipswich; Lauren E. Sears, Bedford, both of Mass.

[73] Assignee: New England Biolabs, Inc., Beverly, Mass.

[21] Appl. No.: 809,267

[22] PCT Filed: Oct. 23, 1995

[86] PCT No.: PCT/US95/13662

§ 371 Date: Mar. 12, 1997

§ 102(e) Date: Mar. 12, 1997

[87] PCT Pub. No.: WO96/12798

PCT Pub. Date: May 2, 1996

Related U.S. Application Data

[63] Continuation-in-part of Ser. No. 329,721, Oct. 25, 1994, abandoned.

[51] Int. Cl.[6] .............................. C12N 9/16; C12N 15/00; C12N 1/20; C07H 21/04
[52] U.S. Cl. .................. 435/196; 435/320.1; 435/252.3; 435/254.11; 435/325; 536/23.2
[58] Field of Search ................................ 435/196, 320.1, 435/252.3, 254.11, 325; 536/23.2

[56] References Cited

U.S. PATENT DOCUMENTS

| 5,210,036 | 5/1993 | Comb et al. | 435/194 |
|---|---|---|---|
| 5,322,785 | 6/1994 | Comb et al. | 435/194 |
| 5,409,811 | 4/1995 | Tabor et al. | 435/6 |

OTHER PUBLICATIONS

Tabor, et al., J. Biol. Chem. 265:8322–8328 (1990).
Richter & Schafer, Eur. J. Biochem., 209:351–355 (1992).
Lahti, et al., Biochimica et Biophysica Acta, 1038:338–345 (1990).
Cooperman, et al., Trends Biochem. Sci., 17:262–266 (1992).
Verhoeven, et al., J. of Bacteriology, 168(1):318–321 (1986).
Kolakowski, et al., Nucl. Acids Res., 16:10441–10452 (1988).
Lahti, et al., J. of Bacteriology, 170(12):5901–5907 (1988).
Kieber and Signer, Plant Molecular Biology, 16:345–348 (1991).
Kasho and Avaeva, Int. J. Biochem., 16(3):315–321 (1984).
Teplyokov, et al., Prot. Sci., 3:1098–1107 (1994).
Cooperan, et al., Methods Enzymol., 87:526–548 (1982).
Josse and Wong in Enzymes, 3rd Ed., vol. 4 (Boyer, P.D., ed.), pp. 499–527 (1971).
Alebeek, et al., Biochim., Biophys. Acta, 1206:231–239 (1994).
Jetten, et al., Arch Microbiol., 157:284–289 (1992).
Richter and Schafer, Eur. J. Biochem. 209:343–349 (1992).
Wakagi, et al., Biochem. Biophys. Acta 1120:289–296 (1992).
Ichiba, et al., J. Biochem. 108:572–578 (1990).
Rapoport, et al., Eur. J. Biochem. 26:237–246 (1972).
Lahti, Microbiol. Review, 47:169–179 (1983).
Schreier and Hohne, FEBS Letters, 90:93–96 (1978).
Hachimori, et al., J. Biochem. 86:121–130 (1978).
Kuranova, et al., Dokl. Akad. Nauk. USSR 295:1013–1016 (1987).
Hohne, et al., Biomed. Biochem. Acta, 47:941–947 (1988).
Tominga, et al., J. Biochem., 81:477–483 (1977).
Howard, et al., Can. J. Biochem., 48:1302–1307 (1970).
Lahti et al. (1990) Conservation of Functional Residues Between Yeast and *E. coli* Inorganic Pyrophosphatases. Biochim. Biophys. Acta 1038: 338–345.

*Primary Examiner*—Robert A. Wax
*Assistant Examiner*—Lisa J. Hobbs
*Attorney, Agent, or Firm*—Gregory D. Williams

[57] ABSTRACT

The present invention provides an extremely thermostable enzyme obtainable from *Thermococcus litoralis*. The enzyme, in inorganic pyrophosphatase (sometimes referred to herein as "PPase"), catalyzes the hydrolysis of inorganic pyrophosphate (PPi) to form two molecules of orthophophate (Pi).

$$P_2O_7^{-4} + H_2O \rightarrow 2HPO_4^{-2}$$

The present invention also provides a purification process for obtaining the inorganic pyrophosphatase from *Thermococcus litoralis*. In addition, characterization of the enzyme reveals a multimeric enzyme (125 kDa) with six identical subunits of 20–21 kDa as revealed by SDS-PAGE. Moreover, the enzyme exhibits unusual stability and maintains 100% of its activity after being incubated at 100° C. in the absence of $Mg^{2+}$ for 4 hours. Furthermore, the complete amino acid and nucleic acid sequence has been obtained; the amino acid sequence shows similarity to known PPase sequences and likely functional residues appear to be conserved. The thermostable enzyme may be native or recombinant and may be used for DNA sequencing or DNA amplification to eliminate the problems of pyrophosphorolysis.

8 Claims, 18 Drawing Sheets

PURITY OF PREPARATIONS OF T. LITORALIS INORGANIC PYROPHOSPHATASE

PURIFICATION OF RECOMBINANT T. LITORALIS INORGANIC PYROPHOSPHATASE

Partial Nucleic Acid and Amino Acid Sequence Of
*T. litoralis* Inorganic Pyrophosphatase

```
       M   N   P   F   H   D
     TTAGAGCCTGGACCGGAAGTACCGGAAGTTG TTTACGCCTTAATAGAGAT TCCAAAGGGG
   1 ----+----+----+----+----+----+----+----+----+----+----+----+ 60
     AATCTCGGACCTGGCC TTCATGGCCTTCAACAAATGCGGAATTATC TCTAAGG TTTCCCC
       L   E   P   G   P   E   V   P   E   V   V   Y   A   L   I   E   I   P   K   G -

AGCAGAAACAAGTATGAGCTTGACAAAAAGACCGGTCTTA TAAAGCTCGATAGAGTTCTT
  61 ----+----+----+----+----+----+----+----+----+----+----+----+ 120
     TCG TCTTT GTTCATACTCGAACTG TTTTT CTGGCCAGAATA TTTCGAGCTATCTCAAGAA
       S   R   N   K   Y   E   L   D   K   K   T   G   L   I   K   L   D   R   V   L -

TACAGNCCATT CCACTACCCGGTCGACTATGGAATCATCCCACAAACATGGTACGATGAT
 121 ----+----+----+----+----+----+----+----+----+----+----+----+ 180
     ATGTCNGG TAAGGTGATGGGCCAGCTGATACCTTAGTAGGGTG TTT GTACCATGCTACTA
       Y   S   P   F   H   Y   P   V   D   Y   G   I   I   P   Q   T   W   Y   D   D -

GACGACCCGTTTGACATCATGGTCATAATGAGGGAGCCGACC
 181 ----+----+----+----+----+----+----+----+-- 222
     CTGCTGGGCAAACTGTAGTACCAGTATTACTCCCT CGGCTGG
       D   D   P   F   D   I   M   V   I   M   R   E   P   T   Y   P   G   V   L
```

```
ATGAATCCATTCCACGATTTAGAGCCTGGACCGGAAGTACCGGAAGTTGTTTACGCCTTA
1   ----+----+----+----+----+----+----+----+----+----+----+----+ 60
    TACTTAGGTAAGGTGCTAAATCTCGGACCTGGCCTTCATGGCCTTCAACAAATGCGGAAT
     M  N  P  F  H  D  L  E  P  G  P  E  V  V  P  E  V  V  Y  A  L

ATAGAGATTCCAAAGGGGAGCAGAAACAAGTATGAGCTTGACAAAAAGACCGGCCTTATA
61  ----+----+----+----+----+----+----+----+----+----+----+----+ 120
    TATCTCTAAGGTTTCCCCTCGTCTTTGTTCATACTCGAACTGTTTTCTGGCCGGAATAT
     I  E  I  P  K  G  S  R  N  K  Y  E  L  D  K  K  T  G  L  I

AAGCTCGATAGAGTTCTTACAGCCCATTCCACTACCGGTCGACTATGGAATCATCCCA
121 ----+----+----+----+----+----+----+----+----+----+----+----+ 180
    TTCGAGCTATCTCAAGAAATGTCGGTAAGGTGATGGGCCAGCTGATACCTTAGTAGGGT
     K  L  D  R  V  L  Y  S  P  F  H  Y  P  V  D  Y  G  I  I  P

CAAACATGGTACGATGATGACGACCCGTTTGACATCATGGTCATAATGAGGAGCCAACA
181 ----+----+----+----+----+----+----+----+----+----+----+----+ 240
    GTTTGTACCATGCTACTACTGCTGGCAAACTGTAGTACCAGTATTACTCCCTCGTTGT
     Q  T  W  Y  D  D  D  D  P  F  D  I  M  V  I  M  R  E  P  T

TATCCGGGAGTTCTTATTGAGGCAAGACCAATAGGCCTCTTCAAGATGATAGACAGCGGC
241 ----+----+----+----+----+----+----+----+----+----+----+----+ 300
    ATAGGCCCTCAAGAATAACTCCGTTCTGGTTATCCGGAGAAGTTCTACTATCTGTCGCCG
     Y  P  G  V  L  I  E  A  R  P  I  G  L  F  K  M  I  D  S  G
```

FIG. 5A

```
       GACAAGGACTACAAGGTATTGGCAGTTCCAGTGGAAGATCCCTACTTT AATGACTGGAAG
301 ----+----+----+----+----+----+ 360
       CTGTTCCTG ATGTTC CATAACCGTCAAGGTCACCTTCTAGGATGAAATTACTGACCTTC

D K D Y K V L  A V P V E D P Y F N D W K

GACATAAGGCGACGTTCCGAAGGCTTTCCTTGACGAGATTGCGCACTTCTTCCAGAGATAC
361 ----+----+----+----+----+----+ 420
       CTGTATTCGCTGCAAGGCTTCCGAAAGGAACTGCTCTAACGGTGAAGAAGGTCTCTATG

D I S D V P K A F L D E I A H F F Q R Y

AAAGAGCTCCAAGGTAAGGAAATCATT GTTGAGGGCTGGGAAAACGCAGAGAAGGCAAAG
421 ----+----+----+----+----+----+ 480
       TTT CTCGAGGTT CCATTCCTT TAGTAACAACTCCGACCCTTTG CGTCTCTTC CGT TTC

K E L Q G K E I I  V E G W E N A E K A K

CAAGAAATACTTAGGGCAATAGAACTTTACAAGGAGAAATTCAAGAAGTGA
481 ----+----+----+----+----+ 531
       GTTCTT TATGAATCCCGTTAT CTTGAAATGTTCCTC TTTAAGTTC TTCACT

Effect of Temperature on the Activity of *T. litoralis* PPase

Effect of pH on the Activity of the Recombinant *T. litoralis* Inorganic Pyrophosphatase Use of Recombinant T. li Inorganic Pyrophosphatase in DNA Sequencing Control - m13mp18, DyePrimer chemistry (-21mer), No PPase + PPase - m13mp18, DyePrimer chemistry (-21mer)
  - 2 NEB units PPase (recombinant)

Expression plasmid pAGR3: 5910 bp.

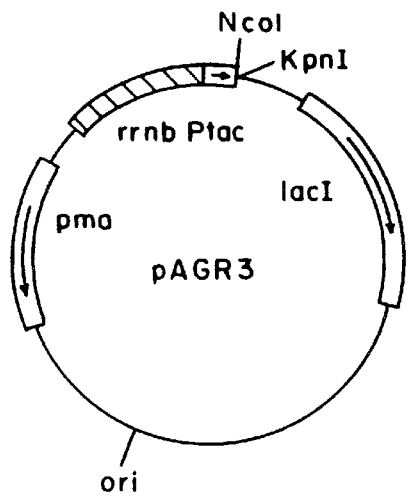

Promoter and Cloning Site Map (SEQ ID NO:28)

```
                 lac operator
    1    GAATTGTGAGCGCTCACAATTCTAGGATGTTAATTGCGCCGACATCATAA -35 region
   51    CGGTTCTGGCAAATATTCTGAAATGAGCTGTTGACAATTAATCATCGGCT -10 region            lac operator                  rbs
  101    CGTATAATGTGTGGAATTGTGAGCGGATAACAATTTCACACAGGAAACAG start
  151    ACCATGGTGAATTCTAGAGCTCGAGGATCCGCGGTACCCGGGCATGCATT
             NcoI   EcoRI  XbaI SacI XhoI BamHI  SacII  KpnI SmaI     BstBI 201    CGAAGCTTCCTTAAGCGGCCGTCGACCGATGCCCTTGAGAGCCTTCAACCA
             HindIII  AflII    EagI  SalI
```

FIG. 15

PURIFIED THERMOSTABLE INORGANIC PYPROPHOSPHATASE OBTAINABLE FROM *THERMOCOCCUS LITORALIS*

CROSS-REFERENCE TO RELATED APPLICATIONS

This application is the national stage application of PCT/US95/13662, which is a continuation-in-part of U.S. application Ser. No. 08/329,721, now abandoned, filed Oct. 25, 1994.

FIELD OF THE INVENTION

The present invention relates to an extremely thermostable enzyme. More specifically, it relates to a thermostable inorganic pyrophosphatase obtainable from *Thermococcus litoralis*, to the recombinant DNA which encodes this enzyme and to the production of this enzyme from the recombinant DNA.

BACKGROUND OF THE INVENTION

Inorganic pyrophosphatase (pyrophosphate phosphohydrolase) (PPase) is an enzyme that plays an important role in energy metabolism. This enzyme is responsible for the hydrolysis of pyrophosphate ($PP_i$) which is formed principally as the product of the many biosynthetic reactions that utilize nucleoside triphosphates, such as DNA and RNA synthesis, coenzyme synthesis and the activation of amino acids and fatty acids. This enzyme is considered to maintain the forward direction of these reactions and is vital for maintaining viability. For a review of microbial inorganic pyrophosphatases, see, Lahti, R., *Microbiol. Review* (1983) 47:169–179, the disclosure of which is hereby incorporated by reference herein.

Inorganic pyrophosphatases occur widely in nature. The two best-studied PPases are those from *Saccharomyces cerevisiae* and *Escherichia coli*. See, for example, Cooperman, B. S., *Methods Enzymol.* (1982) 87:526–548, and Josse, J. and Wong, D. C. K. in *Enzymes* (1971), 3rd Ed., Vol. 4 (Boyer, P. D., ed.) pp. 499–527, Academic Press, New York. Research (the disclosure of which is hereby incorporated by reference herein), has also been conducted on the isolation and purification of inorganic pyrophosphatases from other microorganisms. Four PPases have been isolated from the Archaea: *Methanobacteriun thermoautotrophicum* (strain ΔH) in Alebeek, et al., *Biochim. Biophys. Acta* (1994) 1206:231–239, the disclosure of which is hereby incorporated by reference herein; *Methanothrix soehngenii* in Jetten, et al., *Arch. Microbiol.* (1992) 157:284–289, the disclosure of which is hereby incorporated by reference herein; *Thermoplasma acidophilum* in Richter and Schäfer, *Eur. J. Biochem.* (1992) 209:343–349, the disclosure of which is hereby incorporated by reference herein; and *Sulfolbus acidocaldarius* strain 7 in Wakagi, et al., *Biochim. Biophys.* Acta (1992) 1120:289–296, the disclosure of which is hereby incorporated by reference herein, and *S. acidocaldarius* (DSM 639) in Meyer, et al., *Arch. Biochem. Biophys.* (1995) 319:149–156, the disclosure of which is hereby incorporated by reference herein. Furthermore, the 3-dimensional structure of three PPases has been determined by X-ray crystallography: *Saccharomyces cerevisiae* (Baker's yeast) in Arutiunian, et al., *Dokl. Akad. Nauk. SSSR* (1981) 258:1481, the disclosure of which is hereby incorporated by reference herein; *E. coli* in Kankare, et al., *Protein Engineering* (1994) 7:823–830, the disclosure of which is hereby incorporated by reference herein; and *Thermus thermophilus* in Teplyokov, et al., *Protein Science* (1994) 3:1098–1107, the disclosure of which is hereby incorporated by reference herein.

Two different categories of inorganic pyrophosphatases have been differentiated: soluble (cytoplasmic) and membrane-bound. This differentiation is based not only on cellular localization, but on subunit structure. Cytoplasmic PPases are generally oligomeric proteins consisting of identical subunits. Enzymes from eubacterial and archaeal sources tend to be 19 to 23 kDa subunits and exist as either a tetramer or hexamer. See Alebeek, et al., supra (the disclosure of which is hereby incorporated by reference herein). Dissociation to dimers and trimers has been shown to exist in the absence of divalent cations, Icheba et al., *J. Biochem.* (1990) 108: 572–578. Eucaryotic enzymes are homodimers of 32 to 35 kDa and are exclusively dimers. The only known exception to these rules is the PPase from *Methanothrix soehngenii* that posses an $\alpha_2\beta_2$ subunit structure, Jetten, et al., supra (the disclosure of which is hereby incorporated by reference herein).

All known PPases require the presence of divalent metal cations, with magnesium conferring the highest activity. One exception to this rule is the PPase from *Bacillus subtilis* in which the optimal activity occurs in the presence of $Mn^{2+}$. See Tono and Kornberg, *J. Biol. Chem.* (1967) 242:2375–2382, the disclosure of which is hereby incorporated by reference herein. Kinetic studies have shown that the complex of $Mg^{2+}$ and $PP_i$ ($MgPP_i^{2-}$) is the true substrate and not $PP_i$ alone. The addition of free magnesium ions activates the enzyme by direct binding, while free $PP_i$ is thought to inhibit the enzyme. For details of PPase kinetics, see Rapoport, et al., *Eur. J. Biochem.* (1972) 26:237–246 and Lahti, R., supra (the disclosures of which are incorporated by reference herein).

One interesting feature of this enzyme is its unusual thermostability; the inorganic pyrophosphatase appears to be one of the most thermostable enzymes of an organism. Research has shown that the thermostability of inorganic pyrophosphatases is increased by the presence of divalent cations. Commercially available PPases are heat resistant in the presence of $Mg^{2+}$ up to the following temperatures: *Escherichia coli* (80° C.), *Saccharomyces cerevisiae* (Baker's yeast) (50° C.) and *Bacillus stearothermophilus* (80° C.). Heat resistance is defined as the temperature at which the activity of the enzyme decreases not more than 5% within 10 minutes. See, Schreier, E. and Höhne, W. E., *FEBS Letters* (1978) 90: 93–96, the disclosure of which is hereby incorporated by reference herein.

The thermostability of other inorganic pyrophosphatases has also been studied. The two thermophilic PPases from thermophilic bacterium PS-3 and *Bacillus Stearothermophilus* were found to be thermostable to 75° C. in the presence of $Mg^{2+}$; alone in Tris-HCl buffer these two thermophilic PPases were not intrinsically stable, with the PS-3 PPase losing activity at 40° C. See, Hachimori, et al., *J. Biochem.* (1978) 86:121–130, the disclosure of which is hereby incorporated by reference herein. The PPase from *Sulfolobus acidocaldarius* strain 7 retains complete activity after incubation at 100° C. for 10 minutes in the presence of $MgCl_2$; see, Wakagi, et al., supra. The PPase from *Thermus thermophilus* is heat killed at 96° C. and retains 50% activity after incubation at 90° C. for one hour in the presence of $MgCl_2$; see Kuranova, et al., *Dokl. Akad. Nauk.* SSSR (1987) 295:1013–1016 and Höhne, et al., *Biomed. Biochim. Acta* (1988) 47:941–947, the disclosures of which are hereby incorporated by reference herein. The PPase from *Thiobacillus thiooxidans* retains 90% activity at 80° C. and 40% activity at 100° C. in the presence of $Mg^{2+}$; see, Tominga, N. and Mori, T., *J. Biochem.* (1977) 81:477–483, the disclosure of which is hereby incorporated by reference herein. The PPase from *Thiobacillus ferrooxidans* retains 8% activity after incubation at 100° C. for 60 minutes; see, Howard, A. and Lundgren, D. G., *Can. J. Biochem.* (1970) 48:1302–1307, the disclosure of which is hereby incorporated by reference herein.

Research has been conducted on the effect of pyrophosphorolysis (the reverse reaction of polymerization) and the use of pyrophosphatases in DNA sequencing. Tabor and Richardson, *J. Biol. Chem.* (1990) 265:8322–8328, the disclosure of which is hereby incorporated by reference herein, discovered that pyrophosphorolysis by bacteriophage T7 DNA polymerase can lead to degradation of specific dideoxy-nucleotide-terminated fragments on DNA sequencing gels. The variation in band intensities in a DNA sequencing reaction could be prevented by the addition of inorganic pyrophosphatase to reduce the level of inorganic pyrophosphate. Uniform band intensities are extremely helpful in the analysis of a DNA sequence, particularly with automated DNA sequencers.

Moreover, research has been conducted on the use of inorganic pyrophosphatase to improve the yield of in vitro transcription reactions catalyzed by T7 RNA polymerase. See Cunningham and Ofengand, *Biotechniques* (1990) 9:713–714, the disclosure of which is hereby incorporated by reference herein.

Accordingly, there is a desire in the art to obtain and produce a purified, highly thermostable inorganic pyrophosphatase that may be used to eliminate the problems of pyrophosphorolysis including reactions higher than 37° C. up to 100° C. or higher, in any such process where an accumulation of pyrophosphate could be a problem; for example, any process where DNA polymerases are used in recombinant DNA technology, such as thermal cycle sequencing and primer extension reactions.

SUMMARY OF THE INVENTION

In accordance with the present invention, there is provided an extremely thermostable enzyme obtainable from *T. litoralis* which catalyzes the hydrolysis of inorganic pyrophosphate ($PP_i$) to orthophosphate ($P_i$). The thermostable enzyme obtainable from *T. litoralis* consists of six identical subunits: the molecular mass of the native enzyme as estimated by gel filtration was approximately 125 kDa; the apparent molecular weight for a single subunit was determined to be 20–21 kDa by SDS-PAGE and 19,667 Da by the DNA sequence. The optimum activity can be observed at a temperature of 72° C. which is similar to the temperature (75° C.) for maximum activity of the *T. litoralis* DNA polymerase, also known as Vent$_R$® DNA polymerase (New England Biolabs, Inc.; Beverly, Mass.), which is disclosed in U.S. Pat. Nos. 5,210,036 and 5,322,785, the disclosures of which are hereby incorporated by reference herein. The pH optimum of the enzyme was 9.5 (at 25° C.) in both Tris-HCl and Glycine-NaOH buffers. The thermostable inorganic pyrophosphatase is highly specific for pyrophosphate ($PP_i$) and $Mg^{2+}$. The $K_m$ value for inorganic pyrophosphate was estimated to be 1.0 mM. Furthermore, the inorganic pyrophosphatase is extremely thermostable and exhibits 100% activity after incubation at 100° C. for four hours. The *T. litoralis* PPase has a substantially greater thermal stability than the other commercially available PPases from *Escherichia coli*, *Saccharomyces cerevisiae* (Baker's yeast) and *Bacillus stearothermophilus*.

The DNA encoding for the 20–21 kDa thermostable inorganic pyrophosphatase subunit obtainable from *T. litoralis* has been isolated and provides another means to obtain the thermostable enzyme of the present invention.

BRIEF DESCRIPTION OF DRAWINGS

FIGS. 3A–3B—is an alignment of the *T. litoralis* amino acid sequence of Example II.D. with known amino acid sequences for cytoplasmic pyrophosphatases. Legend: The partial *Thermococcus litoralis* (T.li) amino acid sequence (SEQ ID NO:8) was compared to the alignment of *Saccharomyces cerevisiae* (S.ce) (SEQ ID NO:3), *Arabidopsis thaliana* (A.th) (SEQ ID NO:4), *Escherichia coli* (E.co) (SEQ ID NO:5), thermophilic bacterium PS-3 (SEQ ID NO:6) and *Thermoplasma acidophilum* (T.ac) (SEQ ID NO:7) from Richler, H. and Schäifer, G., *Eur. J. Biochem.* (1992) 209:351–355, the disclosure of which is hereby incorporated by reference herein. Identical amino acid positions are boxed; (•)indicates amino acids considered to be involved in catalytic action.

FIGS. 5A–5B—is the complete DNA sequence (SEQ ID NO:9) of the *T. litoralis* PPase gene and its corresponding amino acid sequence (SEQ ID NO: 10) from Example III.B.. The entire gene is 531 bp which codes for a 176-amino-acid protein.

FIG. 15—is an illustration of pAGR3. pAGR3 was constructed by inserting the EcoRI fragment containing the lacIq gene from pACYC184/lacIq (J. C. Wang, L. J. Peck and K. Becherer (1983) Cold Spring Harbor Symposium 47:85–91, the disclosure of which is hereby incorporated by reference herein) into the EagI site of pRS415 (R. W. Simons, R. Houman and N. Kleckner Gene (1987) 53:85–96, the disclosure of which is hereby incorporated by reference herein) with the lacIq gene in the opposite orientation to the beta-lactamase gene on pRS415. Prior to the ligation, the termini of both DNA fragments were converted to blunt ends using the Klenow fragment of DNA polymerase I. The pRS415/lacIq construct was cleaved with EcoRI and SalI and the fragment bearing the replication origin ligated to a synthetic duplex (below) containing the Ptac promoter, a ribosome binding site, and a mulitple cloning site. This final construct was named pAGR3. Promoter and cloning site map (SEQ ID NO:28). Plasmid pAGR3 is an expression vector which includes several elements:

Figure 1:
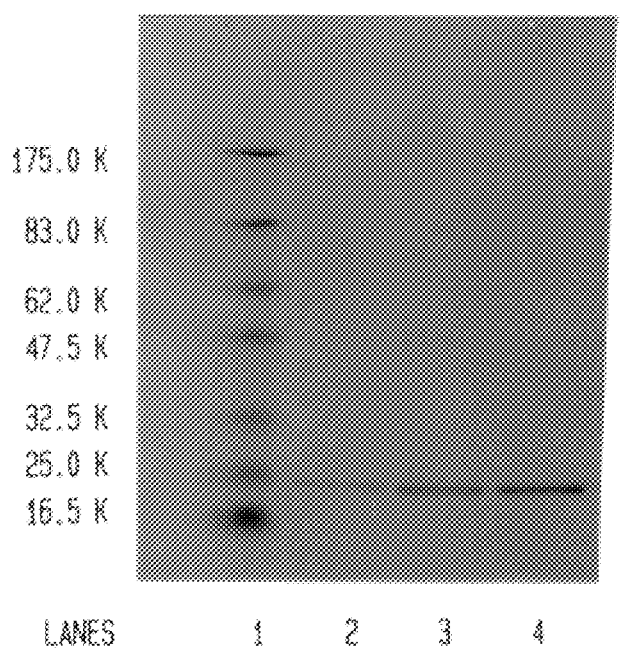
FIG. 1—is a photograph of the SDS-polyacrylamide gel of Example I. Lane 1 shows the molecular weight markers and lanes 2, 3, 4 show the purified *T. litoralis* inorganic pyrophosphatase.

1. A synthetic tac promoter coupled to a symmetric synthetic lac operator sequence;
2. A lac ribosome binding site;
3. A polylier for cloning, with the ATG within the NcoI site being about seven nucleotides downstream of the ribosome binding site;
4. 
5. The replication origin from pBR322;
6. Ampicillin resistance gene; and
7. A four-fold copy of the ribosomal transcription terminator upstream of the tac promoter. These transcription terminators lower the basal level of transcription by reducing read-through transcription from upstream promoters.

DETAILED DESCRIPTION OF THE PREFERRED EMBODIMENTS

The preferred thermostable enzyme herein is an inorganic pyrophosphatase obtainable from *Thermococcus litoralis* strain NS-C (DSM No. 5473). *T. litoralis* was isolated from a submarine thermal vent near Naples, Italy in 1985. This organism, *T. litoralis*, is an extremely thermophilic, sulfur metabolizing archaea, with a growth range between 55° C. and 98° C., Neuner, et al., *Arch. Microbiol.* (1990) 153:205–207, the disclosure of which is hereby incorporated by reference herein. A sample of *T. litoralis* was deposited with the American Type Culture Collection (ATCC) on Sep. 17, 1991 and has received Accession No. 55233.

For recovering the native protein, *T. litoralis* may be grown using any suitable technique, such as the technique described by Belkin, et al., *Arch. Microbiol.* (1985) 142:181–186, the disclosure of which is hereby incorporated by reference herein.

Strain NS-C was routinely grown in 2216 marine broth diluted to ½ strength in synthetic seawater (Turks Island Salts, Merck, 1976). For some of the studies, an artificial seawater medium (ASW) was used, as described by Ruby, et al., *Appl. Environ. Microbiol.* (1981) 42:317–324, the disclosure of which is hereby incorporated by reference herein. In both cases, a vitamin mix (thiamine-HCl, biotin and $B_{12}$, 40 $\mu$g ml$^{-1}$ each), resazurin (0.8 mg l$^{-1}$) and Pipes buffer (20 mM, pH 7.2) were added.

Liquid medium (10 ml, with or without sulfur or organic compounds) was placed in Hungate tubes and flushed for 10 minutes with $N_2$. Na-thioglycolate was then injected to make a 0.02% solution, and the tubes were preincubated at 88° C. After approximately 1 hour, during which the resazurin turned colorless, the medium was inoculated (to $10^6$ cells ml$^{-1}$ with an 18–24 h culture) and the tubes were incubated at 88° C. without shaking. Steam-autoclaved (110° C.) sulfur, when used, was added in 100 mg amounts to 10 ml medium.

After cell growth, one preferred method for isolation and purification of PPase is accomplished using the multi-step process as follows.

First, the cells, if frozen, are thawed, suspended in a suitable buffer such as buffer A (10 mM Tris buffer pH 7.5, 1.0 mM EDTA, 1.0 mM beta-mercaptoethanol), sonicated and centrifuged. The supernatant is then passed through a column which has a high affinity for proteins that bind to nucleic acids such as Affigel blue column (Biorad; Cambridge, Mass.). The nucleic acids present in supernatant solution of *T. litoralis* and many of the proteins including a significant fraction of PPase pass through the column and are thereby pooled by washing the column with several column volumes of low salt buffer (100 mM NaCl) at pH of about 7.5. After washing, a linear gradient such as 0.1 to 2.0M NaCl buffer A is applied to the column; PPase activity is found in the flow through and wash. The Affigel blue flow through/wash (250 ml aliquot) is applied to a $CM^{31}$ Sepharose (cation exchanger) column. The column is washed and eluted with a linear gradient of 0.1 to 1.0M NaCl in buffer A. All PPase is in the flow through/wash. The CM⁻ Sepharose flow through pool is applied directly to a Heparin Sepharose (cation exchanger) column to remove any remaining cations and contaminating DNA. The column is washed and eluted with a linear gradient of 0.1 to 1.0M NaCl. Again 100% of the PPase activity is found in the flow through/wash. The Heparin flow through/wash is applied to a Hydroxylapatite column and washed with 0.1M NaCl buffer A. After washing, the enzyme is eluted with a linear gradient of 0–20% $(NH_4)_2SO_4$. Two peaks contain PPase activity are detected; the peak containing the greatest specific activity for the enzyme is dialyzed against buffer A and applied to a high performance liquid chromatography column (HPLC) mono-Q column (anion exchanger). PPase is again eluted with a linear gradient such as 0.05 to 0.7M NaCl in a buffer A. The fractions having thermostable inorganic pyrophosphatase activity are pooled, dialyzed against 1.2M $(NH_4)_2SO_4$ buffer A and applied to an HPLC phenyl-superose column (hydrophobic). PPase is again eluted with a linear gradient such as 1.2–0M $(NH_4)_2SO_4$ in buffer A. The fractions with enzyme activity are dialyzed against 0.05M NaCl in buffer A and applied to an HPLC Q-HyperD column (Biosepra;

Marlborough, Mass.) (anion exchanger) to concentrate the enzyme. PPase is eluted with a linear gradient such as 0.05 to 0.7M NaCl ,in buffer A. Two peaks contain pyrophosphatase activity with one peak achieving 95% purity at this stage.

The apparent molecular weight of PPase obtainable from *T. litoralis* when electrophoresed on an SDS-polyacrylamide gel (SDS-PAGE) is approximately 20–21 kDa when compared with protein standards of known molecular weight, such as trypsin inhibitor (soybean) assigned a molecular weight of 21,500 Da. It should be understood, however, that as a protein from an extreme thermophile, *T. litoralis* inorganic pyrophosphatase may electrophorese at an aberrant relative molecular weight due to failure to completely denature or other intrinsic properties. The exact molecular weight may be determined from the coding sequence of the *T. litoralis* inorganic pyrophosphatase gene. The apparent molecular weight of 20–21 kDa agrees with reported cytosolic PPases and suggests that the archaea enzyme is similar to most of the eubacterial pyrophosphatases which are composed of four to six identical subunits of 19–21 kDa/monomer. The *T. litoralis* PPase, under non-denaturing conditions, consists of six identical subunits with an approximate molecular weight of 125,500 Da as estimated by gel filtration chromatography using a Superose 12 HR 10/30 (Pharmacia; Piscataway, N.J.) and comparing the elution volumes of several known calibration standards, such as aldolase (rabbit muscle) and bovine serum albumin assigned molecular weight values of 158,000 Da and 67,000 Da respectively.

The PPase activity is measured by following the formation of inorganic pyrophosphate to orthophosphate. Two different methods are used to measure PPase activity in the present invention. The first method was adapted for rapid screening of multiple column fractions and uses thin layer chromatography (TLC). PPase is incubated at 75° C. or 72° C. for 10 to 60 minutes with 25 nmoles inorganic pyrophosphate in a reaction volume of 10 $\mu$l (under oil). NEB CircumVent™ buffer is used (10 mM KCl, 10 mM $(NH_4)_2SO_4$, 20 mM Tris-HCl, 5 mM $MgSO_4$, pH 8.8 @ 25° C.). 1.5 $\mu$l of the reaction is spotted onto a TLC cellulose plate (Merck; Frankfurter, Germany; Product No. 5718) and developed in the following solvent: dioxane (134 ml), distilled water (55 ml), trichloroacetic acid (10 g) and concentrated $NH_4OH$ (0.5 ml). After drying the plate, it is sprayed with 1% ammonium molybdate followed by 1% stannous chloride in 10% HCl. $PP_i$ and $P_i$ are visualized, complete and incomplete reactions can be discriminated. One NEB unit is defined as the amount of enzyme that will convert 25 nmoles inorganic pyrophosphate to orthophosphate at 75° C. in one hour under these conditions.

The second method for assaying PPase activity is a more quantitative measurement of the lmoles of orthophosphate liberated and is an adaptation of the method of Taussky and Schorr, J. Biol. Chem. (1953) 202:675–685, the disclosure of which is hereby incorporated by reference herein. The PPase is incubated at 75° C. for 10 minutes in a 100 $\mu$l reaction containing 30 mM Tris pH 9.0, 1.5 mM $MgCl_2$ and 1.5 mM sodium pyrophosphate. The enzyme is then cooled quickly to room temperature and complexed with 0.9 ml of Taussky-Schorr reagent (5.0 g ferrous sulfate, 10 ml 10% ammonium molybdate in 10N sulfuric acid, in a final solution volume of 100 ml.) After 10 minutes, an absorbance reading is taken at 660 nm. The absorbance reading was compared to a standard curve using Sigma's (St. Louis, Mo.) phosphorous standard (#661–9). One standard unit will liberate 1.0 $\mu$mole of inorganic orthophosphate per minute under the above conditions. Optimal conditions were later determined to be 30 mM Glycine-NaOH, pH 9.5 at 72° C. with a 1:1 ratio of $Mg^{2+}$: $PP_i$ where both $Mg^{2+}$ and $PP_i$ were 1.5 mM.

The PPase of the present invention is extremely thermostable. The enzyme was incubated at 100° C. for four hours in the absence of $Mg^{2+}$ in a 50 mM Tris pH 9.0 buffer. Aliquots were removed at 1, 2, 3, and 4 hours and assayed for PPase activity using the modified method of Taussky and Schorr, supra (the disclosure of which is hereby incorporated by reference herein). 100% of the original activity was detected at 75° C. after the 4 hour incubation. The *T. litoralis* PPase experienced no heat inactivation under the above conditions.

The thermostable enzyme of this invention may also be produced by recombinant DNA techniques, as the gene encoding this enzyme has been cloned from *T. litoralis* genomic DNA. The complete coding sequence for the *T. litoralis* inorganic pyrophosphatase exists as a 531 bp fragment with various engineered restriction sites on each end.

The production of a recombinant form of *T. litoralis* PPase generally includes the following steps: DNA is isolated which encodes the active form of the PPase, either in its native form or as a fusion with other sequences, such as maltose-binding protein (EPO Publication No. 0 286 239, the disclosure of which is hereby incorporated by reference herein), which may or may not be cleaved away from the native form of the PPase and which may or may not effect pyrophosphatase activity. Next, the gene is operably linked to appropriate control sequences for expression in either prokaryotic or eukaryotic host/vector systems. The vector preferably encodes all functions for transformation and maintenance in a suitable host, and may encode selectable markers and/or control sequences for *T. litoralis* PPase expression. Active recombinant thermostable inorganic pyrophosphatase can be recovered either from within host cells or from the culture media if the protein is secreted through the cell membrane.

Each of the above steps can be accomplished in a number of ways. Vectors useful in practicing the present invention should provide varying degrees of controlled expression of *T. litoralis* PPase by providing some or all of the following control features: (1) promoters or sites of initiation of transcription, either directly adjacent to the start of the gene or as fusion proteins, (2) operators which could be used to turn gene expression on or off, (3) ribosome binding sites for improved translation, and (4) transcription or translation termination sites for improved stability. Appropriate vectors used in cloning and expression of *T. litoralis* PPase include, for example, phage and plasmids. Example of phage include lambda gt11 (Promega; Madison, Wis.), lambda Dash (Stratagene; La Jolla, Calif.), lambda ZapII (Stratagene; La Jolla, Calif.). Examples of plasmids include pBR322, pBluescript (Stratagene; La Jolla, Calif.), PAGR3 (FIG. 15), pRRS (Skoglund, et al., *Gene*, (1990) 88:1–5, the disclosure of which is hereby incorporated by reference herein), pSP73 (Promega; Madison, Wis.), pGW7 (ATCC No. 40166) and pET3A (Rosenberg, et al., *Gene*, (1987) 56:125–135, the disclosure of which is hereby incorporated by reference herein).

It was found that one preferred method for cloning the *T. litoralis* inorganic pyrophosphatase involved cloning the PPase gene directly under control of the T7 promotor system in the vector pAII17. However, it will be apparent to those skilled in the art that the preferred mode for practicing the present invention can vary in accordance with techniques known in the art.

Transformation and Infection

Standard protocols exist for transformation, phage infection and cell culture. Sambrook, Fritsch and Maniatis, *Molecular Cloning: A Laboratory Manual*, 2nd Edition (1989), the disclosure of which is hereby incorporated by reference herein. Of the numerous *E. coli* strains which can be used for plasmid transformation, the preferred strains include JM101 (ATCC No. 33876), XL1 (Stratagene; La Jolla, Calif.), and RRI (ATCC No. 31343). *E. coli* strain SL1, ER1578 and ER1458 (Raleigh, et al., *N.A. Research* (1988) 16:1563–1575, the disclosure of which is hereby incorporated by reference herein) are among the strains that can be used for lambda phage, and Y1089 can be used for lambda gt11 lysogeny. When preparing transient lysogens in Y1089 (Arusu, et al., *Experimental Parasitology* (1987) 64:281–289, the disclosure of which is hereby incorporated by reference herein), a culture is infected with lambda gt11 recombinant phage either by a single large dose of phage or by co-culturing with a lytic host. The infected y1089 cells are preferably grown at 37° C. in the presence of the inducer IPTG resulting in build-up of recombinant protein within the lysis-defective host/phage system. Other preferred strains include:

| Strain | Genotype | Reference or construction |
|---|---|---|
| ER2426 | F'proA+B+laqI<sup>q</sup>D(lacZ)M15zzf ::miniTn10(Kan<sup>r</sup>)l-*E. coli* K-12 fhuA2 supE44 e14- rfbD1? relA1? endA1 spoT1? thi-1 D(mcrC-mrr)114::IS10 | NEB #974 Construction: ER2418 X ER2250 -->Kan<sup>R</sup> Aux<sup>+</sup>. |
| ER2497 | F-1DE3 = 1sBamH1o DEcoRI-B int::lacI::PlacUV5::T7 gene1 i21 Dnin5 *E. coli* B fhuA2 [lon] ompT gal sulA11 D(mcrC-mrr) 114::ISO10 R (mcr-73::miniTn10; Tet<sup>s</sup>)2 | NEB #975 Construction: ER2488 X 1DE3 -->i21, nonphage-producing (i.e., Int<sup>-</sup>), supports growth of T7 gene1. |
| ER2504 | F-1DE3 = 1sBamH1o DEcoRI-B int::lacI::PlacUV5::T7 gene1 i21 Dnin5 *E. Coli* B fhuA2[lon] ompT gal sulA11 D(mcrC-mrr)114::IS10R(mcr-73::miniTn10;Tet<sup>s</sup>)2 endA1 R(zgb210::Tn10)Tet<sup>s</sup> | Construction: ER2503-->Tet<sup>s</sup> selection on Bochner plates. |

Construction of Genomic DNA Expression Library and Screening for Thermostable Inorganic Pyrophosphatase The most common methods of screening for a gene of choice are (1) by hybridization to homologous genes from other organisms, (2) selection of activity by complementation of a host defect, (3) reactivity with specific antibodies, (4) screening for enzyme activity or (5) by hybridization to a PCR-generated DNA fragment from the target gene. Screening with a specific antibody was discovered to not be the best approach since a *T. litoralis* PPase antibody raised in rabbit cross-reacted with *E. coli* PPase. The latter method was found to be the best approach with the present invention. However, a method for screening for inorganic pyrophosphatase activity has been developed by Kukko, E., et al. in *FEMS Microbiology Letters* (1982), 15:309–311, the disclosure of which is hereby incorporated by reference herein. This method, the magnesium pyrophosphate overlay test, involves cloning the gene of choice into a mutant *E. coli* K-12 strain (RT4) that produces a low level of PPase. See Lahti, R., et al., *J. Bacteriol.* (1988)170:5901–5907, the disclosure of which is hereby incorporated by reference herein. The colonies are screened rapidly by pouring the following mixture on the colonies: 65 mg $NaN_3$ dissolved in 10 ml of distilled $H_2O$, 0.2 ml of Triton X-100, 2 ml of 50 mM Tris-HCl buffer, pH 8.0 and 2 ml of 50 mM tetrasodium pyrophosphate. 2.5 ml of 0.2 M $MgCl_2$ and 20 ml of hot (100° C.) 2% agar solution in distilled water is added immediately before the mixture was poured on the colonies. After the agar has solidified (about 10 minutes) the plates are incubated at 37° C. Haloes are inspected after 2 hours and 6 hours.

*T. litoralis* DNA can be used to construct genomic libraries as either random fragments or restriction enzyme fragments. The latter approach is preferred. Preferably, Eco RI partial digestion reactions are prepared from *T. litoralis* genomic DNA using standard DNA restriction techniques such as described in Sambrook, Fritsch and Maniatis, supra, the disclosure of which is hereby incorporated by reference herein. Other restriction enzymes such as Bam HI, Nru I, Xba I, Nsi I, Hind III and Pst I can also be used.

Although methods are available to screen both plasmids and phage using DNA probes, in accordance with the present invention, it has been found that phage systems tend to work better with *T. litoralis* and are therefore preferred for the first libraries. Since it is uncertain whether *T. litoralis* control regions function in *E. coli*, phage vectors which supply all necessary expression control regions such as lambda gt11 and lambda Zap II, are preferred. By cloning *T. litoralis* DNA into the Eco RI site of lambda gt11, *T. litoralis* PPase may be expressed either as a fusion protein with beta-galactosidase or from its own endogenous promoter.

Once formed, the expression libraries are screened with a PCR-generated DNA probe using standard hybridization procedures such as described in Sambrook, Fritsch, and Maniatis, supra, the disclosure of which is hereby incorporated by reference herein.

An alternative method is to use inverse PCR on a restriction fragment of *T. litoralis* genomic DNA encoding the gene for the inorganic pyrophosphatase. This method allows one to rapidly amplify the DNA sequences that flank a region of known sequence. See Ochman, H., et al., *Genetics* (1988), 120:621–623, the disclosure of which is hereby incorporated by reference herein.

The *T. litoralis* PPase, coding for all or part of the whole gene, can then be subcloned in, for example, the plasmids pBR322, pRRS, pAGR3, pBluescript, or pUC19. The DNA sequence can be determined by, for example, the Sanger dideoxy chain-terminating method (Sanger, R., Nicklen, S. & Coulson, R. R., *PNAS* (1977) 74:5463–5467), the disclosure of which is hereby incorporated by reference herein. Subcloning into over-expression vector systems (described below) can thus be performed.

Identification of DNA Encoding and Expression of the *T. litoralis* Inorganic Pyrophosphatase Several methods exist for determining that the DNA sequence coding for the *T. litoralis* inorganic pyrophosphatase has been obtained. These include, for example, comparing the amino-terminal sequence of the protein produced by the recombinant DNA to the native protein, or determining whether the recombinant DNA produces a protein which binds antibody specific for native *T. litoralis* PPase. In addition, research by Cooperman, et al., *Trends Biochem. Sci.* (1992) 17:262–266, the disclosure of which is hereby incorporated by reference herein, suggests that the active site of soluble inorganic pyrophosphatases are conserved among many species. X-ray analysis of the *T. thermophilus* PPase shows 15 highly conserved residues that form part of the active site. See Kuranova, et. al., supra. Therefore, by comparing the predicted amino acid sequence of the cloned gene with the amino acid sequence of other known soluble PPases, such as *E. coli*, *S. cerevisiae* and *T. thermophilus*, the identification of these islands of homology provides strong evidence that the recombinant DNA indeed encodes an inorganic pyrophosphatase.

Once identified, the DNA sequence coding for the *T. litoralis* PPase, can be cloned into an appropriate expression vector such as a plasmid derived from *E. coli*, for example, pET3A, pRRS, pAGR3, pBluescript or pUC19, the plasmids derived from the *Bacillus subtilis* such as pUB110, pTP5 and pC194, plasmids derived from yeast such as pSH19 and pSH15, bacteriophage such as lambda phage, bacteria such as *Agrobacterium tumefaciens*, animal viruses such as retroviruses and insect viruses such as Baculovirus.

Over expression of the *T. litoralis* PPase can be achieved, for example, by separating the *T. litoralis* PPase gene from its endogenous control elements and then operably linking the pyrophosphatase gene to a very tightly controlled promoter such as T7 expression vector. See, Rosenberg, et al., *Gene* (1987) 56:125–135, the disclosure of which is hereby incorporated by reference herein. Insertion of the strong promoter may be accomplished by identifying convenient restriction targets near both ends of the *T. litoralis* PPase gene and compatible restriction targets on the vector near the promoter, and transferring the *T. litoralis* PPase gene into the vector in such an orientation as to be under transcriptional and translational control of the strong promoter. Alternatively, PCR can be used to generate desirable sites at both ends of the *T. litoralis* PPase gene for cloning into an appropriate expression vector. Basic methods for cloning PCR-generated fragments include: the incorporation of restriction enzyme sites into deoxyoligonucleotide primers, T/A cloning, ligase-independent cloning, UDG cloning and blunt-ended cloning. See Costa, G. L., et al., *PCR Methods and Applications* (1994) 3:338–345, the disclosure of which is hereby incorporated by reference herein. The strategy of cloning the *T. litoralis* PPase gene into a vector such as pAII17 with a T7 promotor system is the preferred method.

*T. litoralis* PPase may also be overexpressed by utilizing a strong ribosome binding site placed upstream of the *T. litoralis* PPase gene to increase expression the gene. See, Shine and Dalgarno, *Proc. Natl. Acad. Sci. USA* (1974) 71:1342–1346, the disclosure of which is hereby incorporated by reference herein.

The recombinant vector is introduced into the appropriate host using standard techniques for transformation and phage infection. One such appropriate host for a PPase gene is the mutant *E. coli* K-12 strain (RT4), as previously discussed. Another such appropriate host is ER2497/pLysS and ER2504/pLysS in which the pLysS lowers background expression. Methods of transformation are, for example, the calcium chloride method, as described by Cohen, S. N., *PNAS* (1972) 69:2110, the disclosure of which is hereby incorporated by reference herein, is used for *E. coli*. The transformation of Bacillis is carried out according to the method of Chang, S., et al., *Molecular and General Genetic.s* (1979) 168:111, the disclosure of which is hereby incorporated by reference herein. Transformation of yeast is carried out according to the method of Parent, et al., *Yeast* (1985) 1:83–138, the disclosure of which is hereby incorporated by reference herein. Certain plant cells can be transformed with *Agrobacterium tumefaciens*, according to the method describe by Shaw, C. H., et al., *Gene* (1983) 23:315, the disclosure of which is hereby incorporated by reference herein. Transformation of insect cells with Baculovirus is carried out according to, for example, the method described in *Biotechnology* (1988) 6:47, the disclosure of which is hereby incorporated by reference herein.

The transformants are cultivated, depending on the host cell used, using standard techniques appropriate to such cells. For example, for cultivating *E. coli* , cells are grown in LB media (Sambrook, supra) at 30° C. to 42° C. to mid-log or stationary phase. Cells may be induced with IPTG at mid-log or grown to saturation in the case of host cells containing a high copy plasmid, such as pUC18 or pUC19.

The *T. litoralis* PPase can be isolated and purified from a culture of transformed host cells, for example, by either extraction from cultured cells or the culture solution.

When the *T. litoralis* PPase is to be extracted from a cultured cell, the cells are collected after cultivation by methods known in the art, for example, centrifugation. Then, the collected cells are suspended in an appropriate buffer solution and disrupted by ultrasonic treatment, lysozyme and/or freeze-thawing. A crude extract containing the *T. litoralis* PPase is obtained by centrifugation and/or filtration.

When the *T. litoralis* PPase is secreted into the culture solution, i.e., alone or as a fusion protein with a secreted protein such as maltose binding protein, the supernatant is separated from the cells by methods known in the art.

The separation and purification of the *T. litoralis* PPase contained in the culture supernatant or the cell extract can be performed by the method described above, or by appropriate combinations of known separating and purifying methods. These methods include, for example, methods utilizing solubility, such as salt precipitation; methods utilizing the difference in molecular weight, such as dialysis, ultrafiltration, gel-filtration, and SDS-polyacrylamide gel electrophoresis; methods utilizing a difference in electric charge, such as ion-exchange column chromatography; methods utilizing specific affinity, such as affinity chromatography; methods utilizing a difference in hydrophobicity, such as reverse-phase high performance liquid chromatography; methods utilizing a difference in isoelectric point, such as isoelectric focusing electrophoresis; and methods utilizing variations in thermostability, such as heating to denature labile enzymes.

Stabilization and Use of the *T. litoralis* Inorganic Pyronhosphatase

For long-term storage, the thermostable enzyme of the present invention maybe stored in the following buffer: 0.10 M KCl, 20 mM Tris (pH 8.0), 0.1 mM EDTA, 1 mM dithiothreitol and 50% glycerol at −20° C.

The *T. litoralis* PPase of the present invention may be used for any purpose in which such an enzyme is necessary or desirable. For example, in recombinant DNA technology to eliminate the problems of pyrophosphorolysis (the reverse of polymerization). The accumulation of pyrophosphate could be a problem in any process where DNA polymerases are used, such as, second-strand cDNA synthesis in cDNA cloning, DNA sequencing and DNA amplification. See Sambrook, Frtisch and Maniatis, supra, Tabor and Richardson, supra., the disclosures of which are hereby incorporated by reference herein. The procedure of DNA amplification, commonly referred to as polymerase chain reaction (PCR), is disclosed in U.S. Pat. Nos. 4,683,195, 4,683,202 and 4,800,159, the disclosures of which are hereby incorporated by reference herein.

The following Examples are given to illustrate embodiments of the present invention as it is presently preferred to practice. It will be understood that the examples are illustrative, and that the invention is not to be considered as restricted except as indicated in the appended claims.

EXAMPLE I

Purification of a Thermostable Inorganic Pyrophosphatase From *Tizermococcus Litoralis*

*Thermococcus litoralis* strain NS-C (DSM No. 5473) was grown in the media described by Belkin, et al., supra, the disclosure of which is hereby incorporated by reference herein, containing 10 g/l of elemental sulfur in a 100 liter fermentor at its maximal sustainable temperature of approximately 80° C. for two days. The cells were cooled to room temperature, separated from unused sulfur by decanting and collected by centrifugation and stored at −70° C. The yield of cells was 0.8 g per liter.

160 g of cells obtained as described above, were suspended in 550 ml of buffer A (10 mM Tris buffer, pH 7.5, 1.0 mM EDTA, 1.0 mM beta-mercaptoethanol) containing 0.1M NaCl and sonicated for 5 minutes at 4° C. The lysate was centrifuged at 15,000 g for 30 minutes at 4° C. The supernatant solution was passed through a 470 ml Affigel blue column (Biorad; Hercules, Calif.). The column was then washed with 1000 ml of buffer A containing 0.1M NaCl. The column was eluted with a 2000 ml linear gradient from 0.1 to 2.0M NaCl in buffer A; inorganic pyrophosphatase activity was found in the flow through and wash. The Affigel blue flow through/wash (250 ml aliquot) was applied to a 25 ml CM⁻ Sepharose (Pharmacia; Piscataway, N.J.) column, equilibrated with buffer A containing 0.1M NaCl. The column was washed with 50 ml of buffer A containing 0.1M NaCl, and the column was eluted with a 250 ml linear gradient of 0.1 to 1.0M NaCl in buffer A; 100% of the enzyme activity was found in the flow through/wash. The CM⁻ Sepharose flow through/wash pool (300 ml) was applied directly to a 27 ml Heparin Sepharose (Pharmacia; Piscataway, N.J.), equilibrated with buffer A containing 0.1M NaCl. The column was washed with 60 ml of buffer A containing 0.1M NaCl and eluted with a 250 ml linear gradient of 0.1 to 1.0M NaCl; again 100% of the inorganic pyrophosphatase activity was found in the flow through/ wash. The Heparin flow through/wash (360 ml) was applied to a 42 ml Hydroxylapatite (Biorad; Hercules, Calif.) column, equilibrated in buffer A with 0.1M NaCl. The column was washed with 100 ml of buffer A containing 0.1M NaCl. The protein was eluted with a 450 ml gradient of 0 to 20% $(NH_4)_2SO_4$. Fractions were tested for enzyme activity. The inorganic pyrophosphatase activity eluted as two peaks at 8–10 % and 12–15 % $(NH_4)_2SO_4$ respectively; >90% of the enzyme activity applied to the column was found in the second peak. The fractions of the second peak (82 ml) were pooled and dialyzed against 4 liters of buffer A containing 0.05 ml NaCl and then applied to an 8 ml HPLC mono-Q HR 10/10 column (Pharmacia; Piscataway, N.J.). The inorganic pyrophosphatase activity was eluted with a 160 ml linear gradient of 0.05 to 0.7M NaCl in buffer A. The inorganic pyrophosphatase activity eluted as a single peak at 0.27M NaCl. The pooled fractions (4 ml) were diluted to 10 ml with buffer A, dialyzed against 1 liter of buffer A containing 1.2M $(NH_4)_2SO_4$ and applied to an 8 ml HPLC phenyl-superose column (Pharmacia; Piscataway, N.J.). The inorganic pyrophosphatase activity was eluted with a 160 ml linear gradient of 1.2 to 0M $(NH_4)_2SO_4$ in buffer A. The enzyme eluted as a single peak at 0.95 M $(NH_4)_2SO_4$. The pooled fractions (12 ml) were dialyzed into 2 liters of buffer A containing 0.05 ml NaCl and applied to a 2.0 rml HPLC Q-Hyper D column (Biosepra; Marlborough, Mass.). The enzyme was eluted with a 40 ml linear gradient in buffer A from 0.05 to 0.7M NaCl. The enzyme eluted as two peaks at 0.25 and 0.29M NaCl respectively and represented 56% of the original starting activity.

By SDS-polyacrylamide gel electrophoresis (SDS-PAGE) and subsequent staining of the proteins using a colloidal stain (ISS Problue) more sensitive than Coomassie Blue (Neuhoff, et al., *Electrophoresis* (1988) 9:255–262, the disclosure of which is hereby incorporated by reference herein), it was determined that one of the peaks from the Q-Hyper D column was approximately 95% pure with one major band at 20–21 kDa. FIG. 1. The second Q-Hyper D peak was approximately 50% pure with two major bands present, one at 50 kDa and the other at 20–21 kDa. These molecular weight determinations were obtained by comparison on the same gel to the migration of the following pre-stained marker proteins (New England Biolabs, Inc.: Beverly, Mass.): MBP-β-galactosidase, 175,000 Da; MBP-paramyosin 83,000 Da; glutamic dehydrogenase, 60,000 Da; aldolase, 47,500 Da; triosephophate isomerase, 32,500 Da; β-lactoglobulin A; 25,000 Da, lysozyme, 16,500 Da; and aprotinin, 6,500 Da. At this level of purification the inorganic pyrophosphatase had a specific activity of 1,400,000 NEB units (or approximately 13,000 standard units) of pyrophosphatase activity per mg of pyrophosphatase protein and represented 56% of the total activity present in the Affigel blue flow through/wash.

EXAMPLE II

Cloning of *T. Litoralis* Inorganic Pyrophosphatase

A. Identification of Amino Acid Sequence from the Purified *T. litoralis* Inorganic Pyrophosphatase The *T. litoralis* pyrophosphatase, prepared as described above, was subjected to electrophoresis and electroblotted according to the procedure of Matsudaira, P., *J. Biol. Chem.* (1987) 262:10035–10038, the disclosure of which is hereby incorporated by reference herein, with modifications as previously described. See Waite-Rees, T. A., et al., *J. Bacterol.* (1991) 173:5207–5219 and Looney, M. C., et al., *Gene* (1989) 80:193–208, the disclosures of which are hereby incorporated by reference herein. The membrane was stained with Coomassie blue R-250 and the protein band of approximately 20–21 kDa was excised and subjected to sequential degradation (Looney, M. C., et al., supra, the disclosure of which is hereby incorporated by reference herein). The amino terminal sequence of the PPase was obtained using an Applied BioSystems Division, Perkin-Elmer Corporation (Foster City, Calif.) 470A protein sequencer, Brooks, et al., *Nucleic Acid Research* (1989) 17:979–997, the disclosure of which is hereby incorporated by reference herein. The first 37 amino acid residues (SEQ ID NO: 11) of the 20–21 kDa protein corresponded to: Met-Asn-Pro-Phe-His-Asp-Leu-Glu-Pro-Gly-Pro-Glu-Val-Pro-Glu-Val-Val-Tyr-Ala-Leu-Ile-Glu-Ile-Pro-Lys-Gly-Ser-Arg-Asn-Lys-Tyr-Glu-Leu-Asp-Lys-Lys-Thr.

An additional sample of the *T. litoralis* inorganic pyrophosphatase, 5 μg in 20 μl, was treated with 1 mg of cyanogen bromide (Sigma; St. Louis, Mo.) dissolved in 200 μl of 88% distilled formic acid for 24 hours in the dark at room temperature. This reaction mixture was evaporated to dryness and resuspended in 100 μl of 5% trifluroacetic acid (TFA) in water. This sample was injected on an Applied BioSystems Division, Perkin-Elmer Corporation (Foster City, Calif.) (ABI 172 microbore HPLC system containing a 2.1×250 mm, 5 μm particle 300 Å pore size C18 column (Vydac; Hesperia, Calif.) equilibrated at 95% solvent A (water, 0.1% TFA) and 5% solvent B (acetonitrile, 0.1% TFA). The column was developed at flow rate of 200 μl/min with UV detection at 214 nm for 2 minutes followed by a 45 minute linear gradient from 5% B to 60% B and a 10 minute linear gradient from 60% B to 100% B. The major peptide peaks were collected and subjected to sequential degradation (Looney, M. C., et al., supra). The first 18 amino acid residues of the peptide designated C41–19 corresponded to Arg-Glu-Pro-Thr-Tyr-Pro-Gly-Val-Leu-Ile-Glu-Ala-Arg-Pro-Ile-Gly-Gly-Phe (SEQ ID NO:12). Residues 13 and 17 were somewhat ambiguous. This fragment was therefore determined not to be derived from the N-terminus of the protein.

B. Preliminary Mapping of the *T. litoralis* Inorganic Pyrophosphatase

Based on the N-terminus sequence, two 17-oligomers were synthesized on an Applied BioSystems' automated DNA synthesizer (Applied BioSystems Division, Perkin-Elmer Corporation; Foster City, Calif.) with the following sequences: 5' Bt-ATGAAYCCNTTYCAYGA 3' (probe 109–129) (SEQ ID NO:13); and 5' Bt-ATHGARATHCCNAARGG 3' (probe 109–130) (SEQ ID NO:14). (Y=C or T; N=A, C, G, or T; H=A, C or T; R=A or G). Based on the internal sequence from the cyanogen bromide treatment, a 23-mer was made of the following complementary DNA sequence: 5' Bt-AGNACNCCNGGRTANG TNGGYCC 3' (probe 110–144) (SEQ ID NO: 15). The oligomer probes were end labeled with biotin (Bt) using a biotinylated phosphoroamidite (Applied BioSystems Division, Perkin-Elmer Corporation; Foster City, Calif.)

The three southern blots were prepared as follows: 200 ng of *T. litoralis* genomic DNA was digested with the restriction endonucleases EcoRI, HindIII, and Pst I. The digests were electrophoresed on a 1.0% agarose gel. The gel was washed in 0.25M HCl for 30 minutes, then in two changes of 0.5M NaOH, 1.5M NaCl for 15 minutes each and finally in two changes of 0.5M Tris pH 7.5, 1.5M NaCl for 15 minutes each. The DNA was transferred to nylon membrane, Immobilon™-S (Millipore: Bedford, Mass.), using recommended protocols for the MilliBlot™-VP Vacuum Pump (Millipore; Bedford, Mass.). The membrane was presoaked in 2× SSC and 20× SSC (175.3 g NaCl, 88.2 g sodium citrate in 1 L of $H_2O$) was used as the transfer buffer. The DNA transfer was allowed to proceed for approximately one hour. The membrane was dried for 30 minutes at 45° C. and ultraviolet crosslinked at 254 nm using a power output of 33.00 $mJ/cm^2$ for 30 seconds with the X-linker-254 (Automated BioSystems, Inc. (Essex, Mass.)/Owl Scientific, Inc. (Woburn, Mass.)).

The nylon blot was pre-hybridized in 5 ml of 6× SSC, 5× Denhardt's reagent (0.5 gram ficoll, 0.5 gram polyvinylpyrrolidone, 0.5 gram bovine serum albumin), 0.5% SDS and 100 μg/ml denatured sonicated salmon sperm DNA. After prehybridizing at 42° C. for one hour, the biotinylated labeled probe was added and the hybridization was carried out at 42° C. overnight. The blot was washed with two changes of 2× SSC, 0.1 % SDS at room temperature for 5 minutes each; two changes of 1× SSC, 0.1% SDS at 42° C. for 15 minutes each and finally two changes of 1× SSC at room temperature for 5 minutes each. The blot was developed using chemiluminescent detection according to the standard protocol in NEBlot™ Phototope Detection Kit (New England Biolabs, Inc.; Beverly, Mass.). The blots were exposed to X-ray film (XAR5, Kodak; Rochester, N.Y.) for 20 minutes.

Results of autoradiography of the above blots revealed high degeneracy of probes to be a possible source of difficulty in specifically cloning this PPase.

C. Using PCR to Amplify Part of the Inorganic Pyrophosphatase Gene from *T. litoralis* Genomic DNA Based on the determined amino acid sequence of the protein (SEQ ID NO: 11), new primers were designed for PCR. In order to reduce the primer degeneracy, deoxyinosine was substituted in all places where the third position of the amino acid was completely ambiguous (A, C, G or T). The primer for the N-terminal was as follows: 5° CTGAAT-TCCATATGAAYCCNTTYCAYGA 3' (primer 115–70) (28-mer) (SEQ ID NO:16); Eco RI and Nde I recognition sites were added to the 5' terminus to facilitate cloning; incorporation of one deoxyinosine reduced the degeneracy from 32-fold to 8-fold. The sequence of the internal primer was: 5' AGNACNCCNGGRTANGTNGGYCC 3' (primer 115–71) (23-mer) (SEQ ID NO: 17); the degeneracy of the internal primer was reduced from 4096-fold to 4-fold with the incorporation of 5 deoxyinosine residues (N =deoxyinosine; Y=C or T; R=A or G).

The *T. litoralis* inorganic pyrophosphatase gene fragment was amplified using PCR under the following reaction conditions. A 100 ml reaction contained 100 ng of genomic *T. litoralis* DNA, 1× Taq buffer (50 mM KCl, 10 mM Tris-HCl, pH 9.0 @ 25° C., 0.1% Triton X-100, 2.5 mM $MgCl_2$), 200 mM dNTP's, the primers 115–70 and 115–71, and 2.5 units of Taq DNA polymerase. The PCR reaction was run on a thermal cycler for forty cycles of denaturing at 95° C. for 1 minute, annealing at 35° C. for 1 minute and extending at 72° C. for 1 minute. A single 265 bp PCR product was obtained. No PCR products were obtained at annealing temperature of 40° C. and 45° C. The PCR product was purified using a Centricon-100 (Amicon; Danvers, Mass.) according to manufacturer's recommendation. Final concentration of the purified PCR fragment was approximately 15 ng/ml with a total yield of 1.5 mg in a 100 ml volume.

D. Identification of Partial Nucleic Acid Sequence of the *T. Litoralis* Inorganic Pyrophosphatase Gene The PCR fragment was sequenced on a thermal cycler using the two PCR primers (115–70 and 115–71), from Example II.C and primer 109–130, described in Example II.B. All three reactions were sequenced according to standard Applied BioSystems Division, Perkin-Elmer Corporation (Foster City, Calif.) Taq Dyedeoxy™ Terminator Cycle Sequencing Kit protocols. Sequencing reactions were set up as follows: 9.5 μl reaction pre-mix (16 μl 5× TACS Buffer, 4 μl dNTP Mix, 4 μl each of DyeDeoxy Terminators (A, G, C and T) and 2 μl AmpliTaq® DNA Polymerase), 7.0 μl purified PCR fragments and 3.2 pmol primer in a reaction volume of 20 μl. The sequencing reactions were cycled under the following conditions: preheat cycler to 95° C. for 5 minutes, 25 cycles of 1 minute denaturing at 95° C., 2 minutes annealing at 35° C. and I minute extension at 72° C. Extension products were purified using Centri-Sep spin columns (Princeton Separation Sciences; Princeton, N.J.) following the recommended spin column purification protocol. Samples were run on an Applied BioSystems Division, Perkin-Elmer Corporation (Foster City, Calif.) 373A Automated DNA Sequencer. Data was analyzed using the Applied BioSystem Division, Perkin-Elmer Corporation (Foster City, Calif.) Mac-Assembler Computer Programs (Factura™ and AutoAssembler™).

Figures 1, 13A:
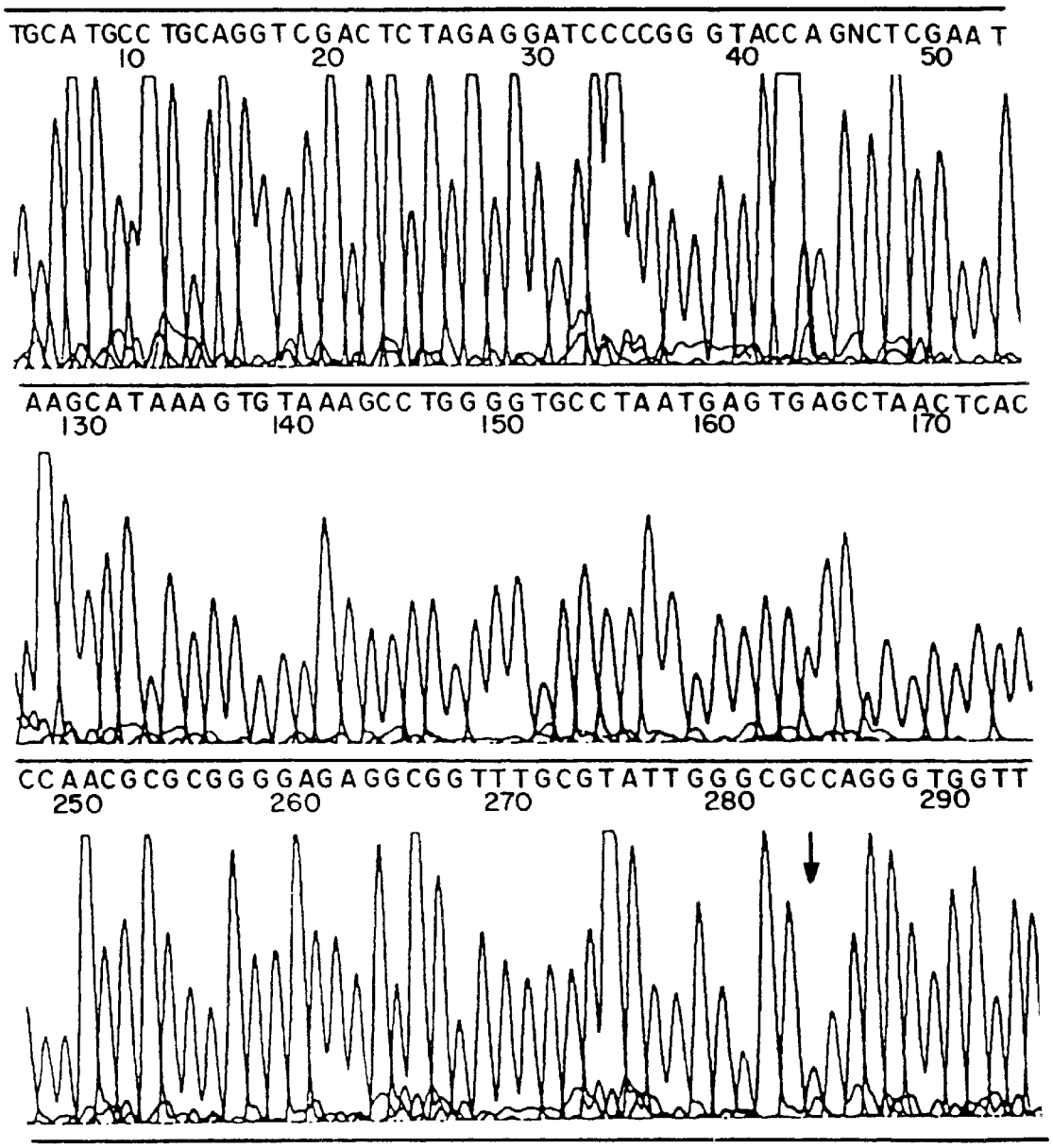
FIGS. 13A–13B—is partial trace data from m13mp18 sequenced with AmpliTaq DNA polymerase (Applied BioSystems Division, Perkin-Elmer Corporation; Foster City, Calif.) with and without the addition of T. litoralis PPase of example VII. The data shown in panel (13A-1 and 13A-2) (partial trace data from an m13mp18 template sequenced with AmpliTaq DNA polymerase (Applied BioSystems Division, Perkin-Elmer Corporation; Foster City, Calif.) (no T. litoralis PPase)) was produced without the addition of PPase and contains a weak Guanine (G) peak at position 164 and a missing G peak, miscalled as Unknown (N), at position 310. When the same m13mp18 template in panel (13B-1 and 13B-2) (partial trace data from an m13mp18 template sequenced with AmpliTaq DNA polymerase (Applied BioSystems Division, Perkin-Elmer Corporation; Foster City, Calif.) in the presence of T. litoralis inorganic pyrophosphatase) is sequenced with the addition of PPase (one NEB unit, NEB=New England Biolabs, Inc.; Beverly, Mass.), the peaks are resolved.
Figures 2, 13A:
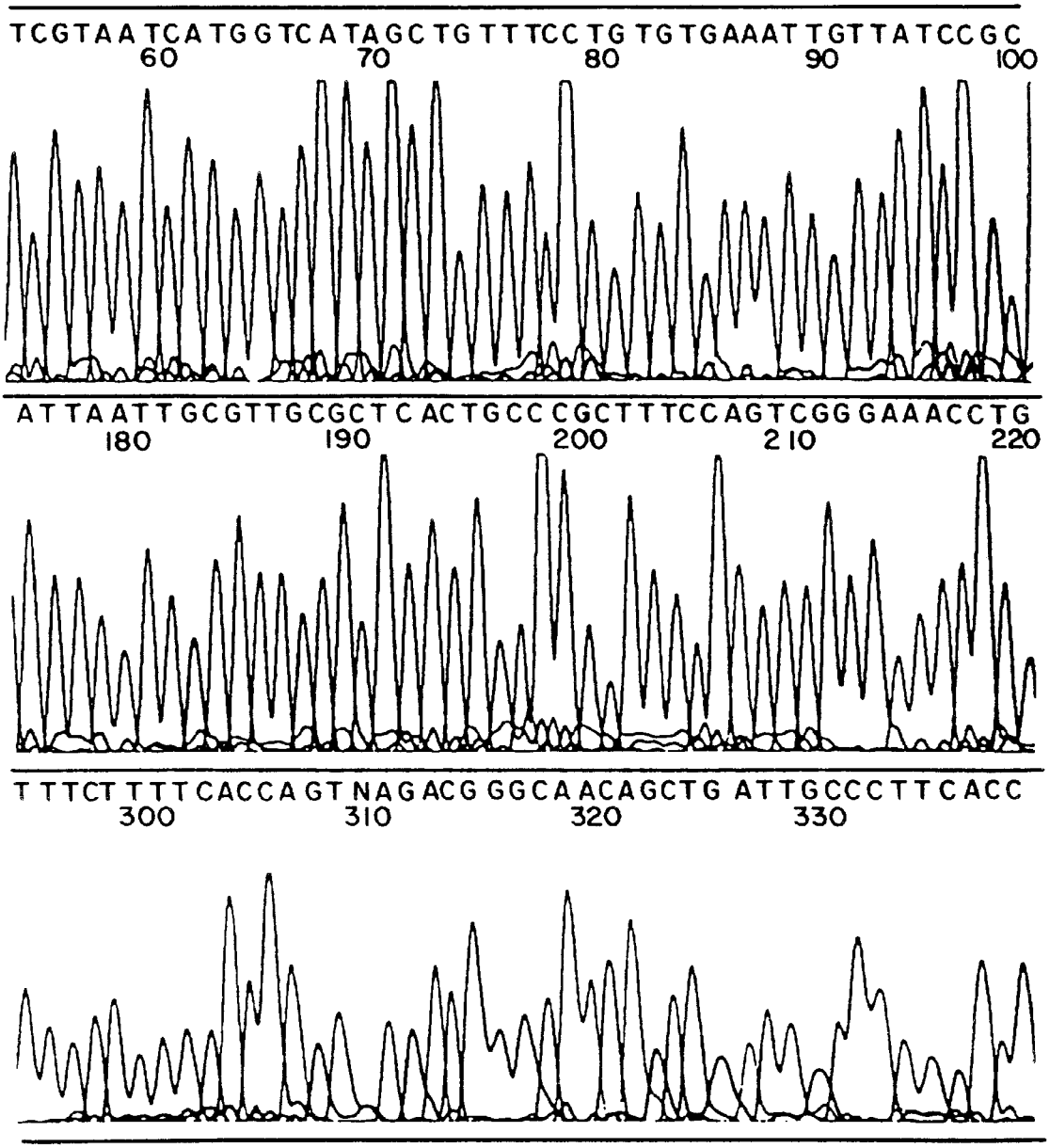
FIG. 2—is the partial DNA sequence (SEQ ID NO:1) of the *T. litoralis* PPase gene and its corresponding amino acid sequence (SEQ ID NO:2) of Example II.D.; the DNA sequence was obtained from a PCR-generated fragment. Highlighted in bold lettering are: (1) the N-terminal and C-terminal amino acid sequences used to prepare degenerate primers for both PCR and DNA sequencing; (2) an internal amino acid sequence used to prepare a third primer for DNA sequencing.
Figures 1, 13B:
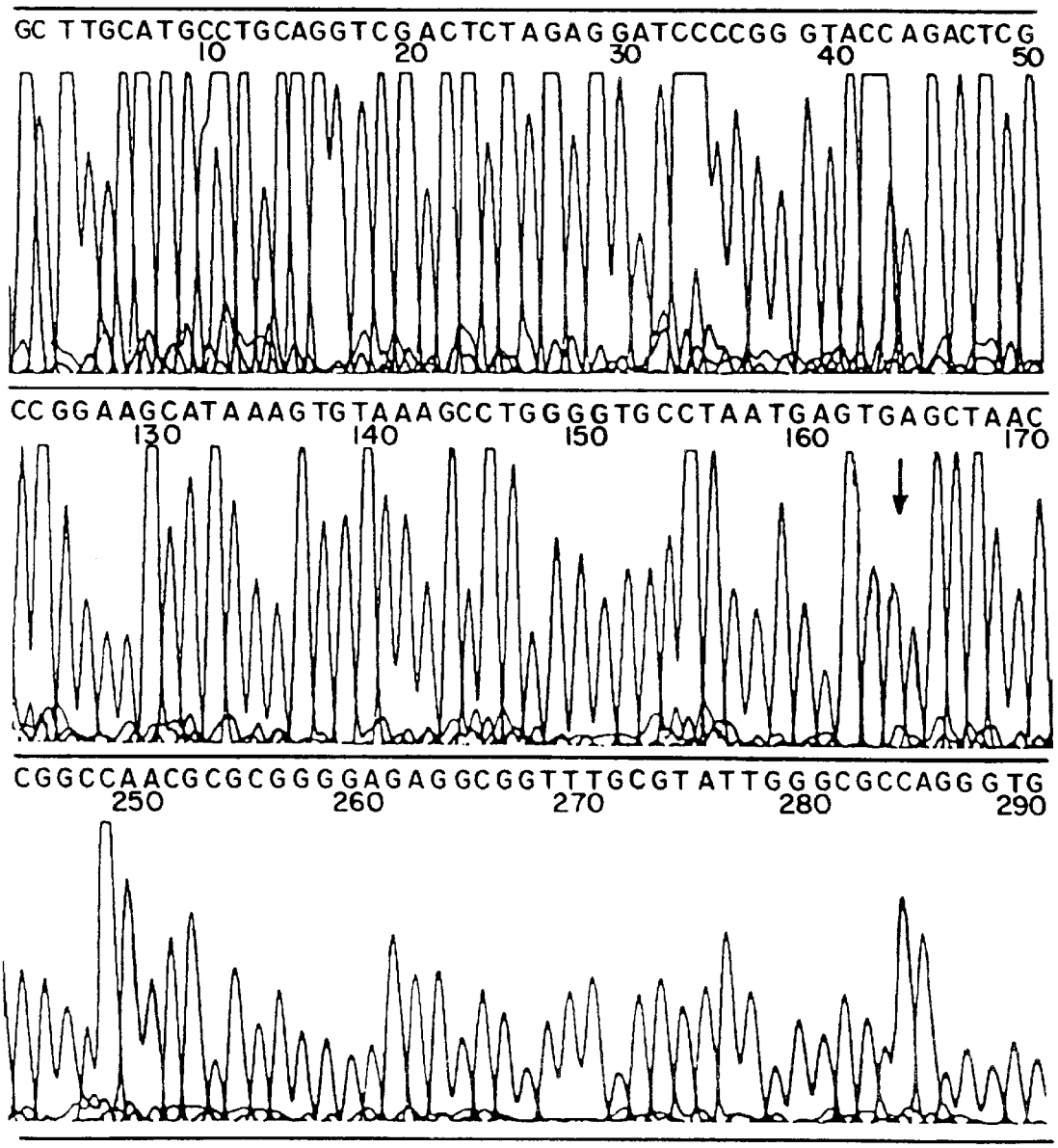
Figures 2, 13B:
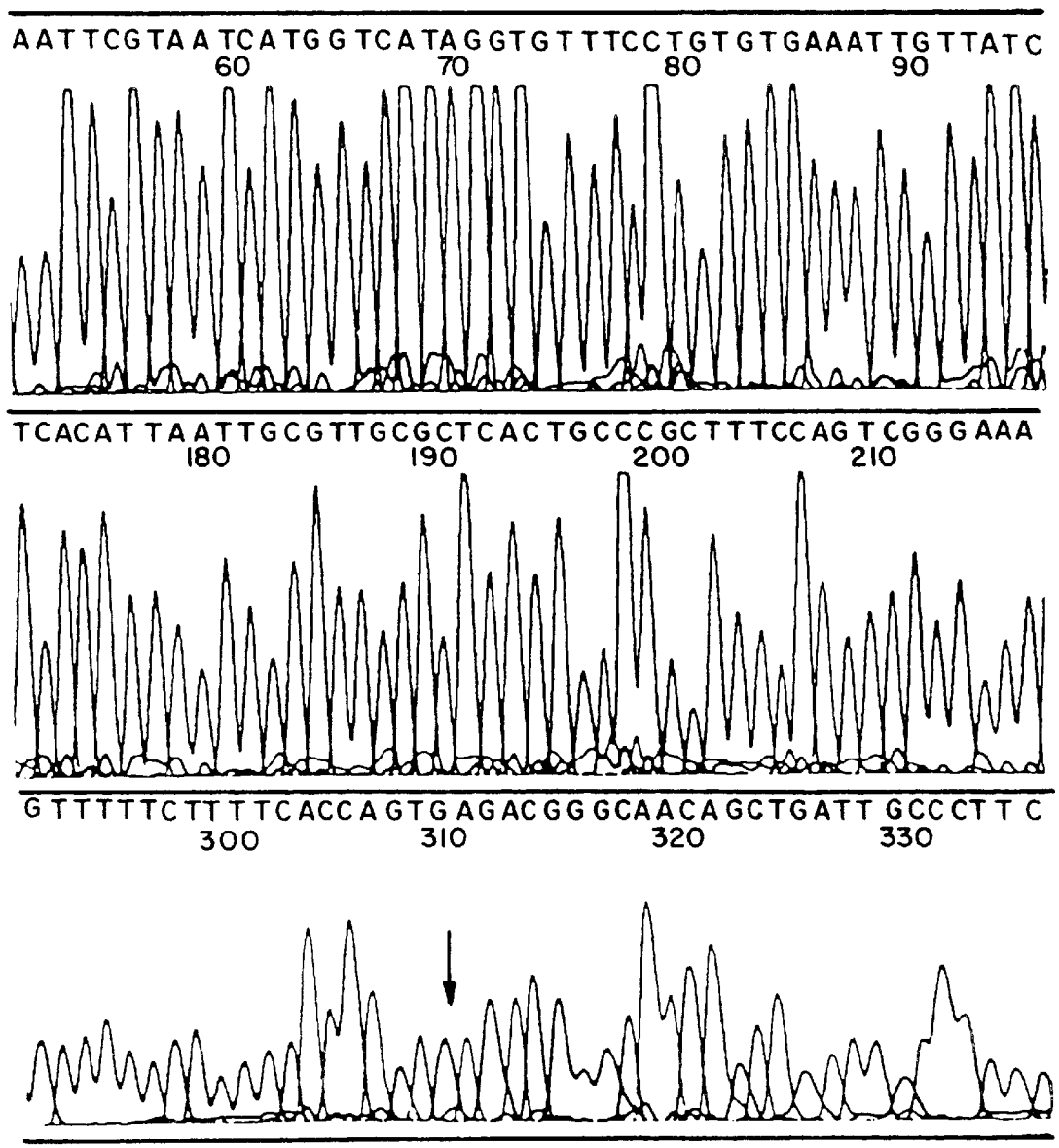

The consensus sequence of the PCR-generated fragment plus its corresponding amino acid sequence can be seen in FIG. 2. Comparison of the amino acid sequence with other known inorganic pyrophosphatases showed homology. Studies of evolutionary conservation among the known amino acid sequences for soluble inorganic pyrophosphatase have shown that only functional residues appear to be conserved, while other residues are more distantly related. See Cooperman, et al., *Trends Biochem. Sci.* (1992) 17:262–266, the disclosure of which is hereby incorporated by reference herein. Comparison of the partial amino acid sequence for the *T. litoralis* PPase with the alignment of sequences for *S. cerevisiae, A. thaliana, E. coli*, PS-3 and *T. acidophilum* in Richter and Schäfer, *Eur. J. Biochem.* (1992) 209:351–355, the disclosure of which is hereby incorporated by reference herein, showed conservation in the same regions. See FIG. 3.

E. Obtaining and Cloning the Complete *T. litoralis* Inorganic Pyrophosphatase

PCR has identified the DNA fragment coding for the amino terminal half of the *T. litoralis* inorganic pyrophosphatase. In order to find a fragment large enough to code for the entire gene, restriction enzyme digests of *T. litoralis* genomic DNA were prepared and were used for probing with the PCR fragment. Restriction enzyme digests were performed in separate tubes. Each reaction contained 2 μg of *T. litoralis* DNA in a total reaction volume of 50 μl. Each enzyme (all from New England Biolabs, Inc.; Beverly, Mass.) was used in conjunction with its recommended reaction buffer. Each reaction contained 20 units of enzyme, after incubation for 60 minutes, another 20 units was added and the reaction was incubated further for 60 minutes. The following digests were performed: Bam HI, Eco RI, Hind III, KpnI, Pst I, Sac I, Sac II, Sal I, Sma I, Sph I and Xba I. All digests were performed at 37° C. except for Sma I which was incubated at 25° C. Digests were electrophoresed on an agarose gel and transferred to nylon membrane, Immobilon™-S (Millipore: Bedford, Mass.) using the method described in example II.B. The PCR product was labeled with biotin according to the recommended protocol in NEBlot™ Phototope Detection Kit (New England Biolabs, Inc.; Beverly, Mass.). The membrane was probed with the biotinlabeled PCR fragment and hybridization was detected with an enzyme catalyzed light-emitting reaction according to the recommended protocol in NEBlot™ Phototope Kit (New England Biolabs, Inc.; Beverly, Mass.) The released light was subsequently captured on X-ray film. The resulting banding pattern revealed single fragments large enough to encode the entire inorganic pyrophosphatase gene (approximately 1.5 –3 kb). Digests in which the biotin-labeled PCR fragment hybridized to fragments large enough to contain the entire PPase gene were Bam HI (approximately 1600 bp), Eco RI (approximately 1800 bp), HindIII (approximately 870, 1500 bp), Pst I (approximately 3500 bp) and Sac I (approximately 1300 bp). All other digests revealed fragments greater than 4000 bp.

Bam HI, Eco RI and Xba I *T. litoralis* secondary libraries already exist at New England Biolabs, Inc. (Beverly, Mass.) for screening, as described in U.S. Pat. Nos. 5,210,036 and 5,322,785, the disclosures of which are hereby incorporated by reference herein. Alternatively, new libraries can be constructed using standard techniques as described in Sambrook, Fritsch and Maniatis, supra, the disclosure of which is hereby incorporated by reference herein.

An alternative approach is to use inverse PCR on a restriction fragment of *T. litoralis* genomic DNA encoding the entire gene for the inorganic pyrophosphatase. This approach would allow the rapid amplification of the DNA sequence that flanks the 265 bp region of known sequence. See Ochman, H., et al., *Genetics* (1988), 12:621–623, the disclosure of which is hereby incorporated by reference herein.

Bam HI Library

A Bam HI genomic library was constructed using λ DashII. λ DashII is a Bam HI substitution vector that can be used to clone 10–20 kb Bam HI DNA fragments. 25–75 nanograms of *T. litoralis* genomic DNA digested with Bam HI was ligated to 0.5 μg Bam HI digested, calf intestine phosphatase treated λ DashII DNA in 5.0 μl of strand ligation buffer including 0.5 μl T4 DNA ligase (New England Biolabs, Inc. No. 202). Three μl of the ligation reaction were packaged using Gigapack Plus (Stratagene; La Jolla, Calif.) according to the manufacturer's instructions. After incubation at room temperature for two hours, the packaged phage were diluted in 500 μl of SM buffer (SM buffer=100 mM NaCl, 8 mM MgSO$_4$, 50 mM Tris pH 7.5, 0.01% gelatin) plus three drops chloroform. The packaged Bam HI library was called sample V96. *E. coli* strain ER1458 was used for phage infection.

Mixed Partial λgt11 Expression Library

A mixed partial genomic library was constructed using λgt 11. *T. litoralis* DNA was partially digested with 7 different restriction enzymes (Alu I, Dra I, HaeIII, Hinc II, Pvu II, Rsa I and Ssp I) in the following manner: 4.0 μg of *T. litoralis* DNA was digested at 37° C. with 5.0 units of each enzyme in separate 40 μl reactions containing a 50 mM NaCl buffer (10 mM Tris pH 7.5, 50 mM NaCl, 10 mM MgCl$_2$ and 5 mM BME). Three pl of 100 mM EDTA was added to 15 μl samples at 30, 45 and 60 minutes. 0.2 μg of each digest was electrophoresed on an agarose gel to monitor the extent of digestion. Approximately 31 μg of *T. litoralis*

DNA partials were pooled to form the "mixed partial pool", all reactions were used except the Rsa I (45 minutes) and Ssp I (30 minutes) digests; the pool was then heated at 65° C. for 15 minutes.

40 μl of the mixed partial pool were ligated to various linkers using standard ligation buffer (ligation buffer=66 mM Tris pH 7.5, 1 mM ATP, 1 mM spermidine, 10 mM $MgCl_2$, 15 mM DTT, and 2 mg/ml gelatin), 2 μl T4 polynucleotide kinase (NEB No. 201) and 10 μl T4 DNA ligase (NEB No. 202). The ligation was performed at 16° C. overnight. This ligation reaction was processed by phenol/chloroform extraction, ethanol precipitation and run over a Sepharose CL 4B column. 0.5 μl of fraction 11 from the Sepharose CL 4B column was ligated to 0.28 mg of EcoRI cut, bacterial alkaline phosphatase treated ,λgt 11 DNA in a 5.0 μl reaction using the standard ligation buffer, as described above, and 1.0 μl T4 DNA ligase (NEB No. 202). The ligation was performed at 16° C. overnight. 4 μl of this ligation reaction were packaged using Gigapack Gold (Stratagene; La Jolla, Calif.) according to the manufacturers instructions. After incubation at room temperature for two hours, the packaged phage were diluted in 500 μl of SM (SM=100 mM NaCl, 8 mM $MgSO_4$, 50 mM Tris pH 7.5, 0.01% gelatin) plus three drops of chloroform. The packaged mixed partial library was called sample V6-5 and consisted of $1 \times 10^4$ individual phage. $E.$ $coli$ strain ER 1458 was used for phage infection.

Screening of the Mixed Partial and BanI HI Libraries and Subcloning of Inserts

The Bam HI λ DashII and mixed partial λgt11 phage libraries were screened according to standard protocols using the PCR product from Example II.B. radiolabeled with $\alpha^{32}P$. 20 phage (D1 through D10 and G1 through G10) which reacted with the probe were picked and 8 were plaque purified.

The 8 PCR-probe positive phage were used to lysogenize $E.$ $coli$ 1458. Plate lysate was prepared and phage DNA was purified from liquid culture using Qiagen-tip 20 columns (Qiagen; Chattsworth, Calif.) according to the manufacturer's recommended protocol for lambda DNA purification. DNA from each λDash II phage (D1-A, D2-A, D3-A) were digested with Bam HI, while DNA from each λgt 11 phage (G1-A, G2-A, G3-A, G4-A) were digested separately with Eco RI and Bsi WI. Double digesting the λgt11 with Kpn I/Sac I to liberate a DNA fragment containing inserted DNA at the Eco RI restriction site was not possible since the PPase gene contains internal Sac I sites, as discovered in Example II.D.. 20 units of each enzyme (all from New England Biolabs, Inc.; Beverly, Mass.) was used in conjunction with its recommended reaction buffer in a volume of 50 μl and incubated at 37° C. for six hours. Digests were electrophoresed on a 1% agarose gel and transferred to nylon membrane, Immobilon™-S (Millipore; Bedford, Mass.) using the method described in Example II.B.. The PCR product of Example II.C. was labeled with biotin according to the recommended protocol in NEBlot™ Phototope Detection Kit (New England Biolabs, Inc.; Beverly, Mass.). The membrane was probed with the biotin-labeled PCR fragment and hybridization was detected with an enzyme catalyzed light-emitting reaction according to the recommended protocol in NEBlot™ Phototope Detection Kit (New England Biolabs, Inc.; Beverly, Mass.). The released light was subsequently captured on X-ray film. The resulting banding pattern revealed single fragments that agreed with the Southern blot analysis of genomic $T.$ $litoralis$ DNA of Example II.E. and were large enough to encode the entire inorganic pyrophosphatase gene (approximately 1.5–3.0 kb). Fragments that were large enough to contain the entire PPase gene were D1A/Bam HI (approximately 1600 bp), D3A/Bam HI (approximately 1600 bp), G1A/Eco RI (approximately 1500 bp), G4A/Eco RI (approximately 3000 bp) and G1A/Bsi WI (approximately 2000 bp).

The above fragments were reobtained by digesting four times the amount of phage DNA as described above in a reaction volume of 100 μl with 10 μl of each restriction enzyme (New England Biolabs, Inc.; Beverly, Mass.). The complete digests were run on a 1% agarose gel and excised from the agarose using GENE-CLEAN® II, according to the manufacturer's recommended protocol (Bio101; Vista, Calif.). A 2 μl sample of each of the 5 purified phage DNA inserts were run on a 1% agarose gel to check recovery.

Each insert (0.08 pmoles) was ligated to calf intestinal alkaline phosphatase (CIAP) treated pUC19 (0.016 pmoles) digested with Bam HI, Eco RI or Acc 65I to give compatible ends in a 20 μl volume containing standard ligation buffer, as described above, and 5 units T4 DNA ligase (New England Biolabs, Inc.; Beverly, Mass., Product No. 202). The ligation was performed at 16° C. overnight. ER2426 competent cells (Sambrook, Fritsch and Maniatis, supra, the disclosure of which is hereby incorporated by reference herein) were transformed with the ligation mixture. Of 28 recombinants examined, three looked promising; clones F10, F14 and F22 contained inserts large enough to contain the entire $T.$ $litoralis$ inorganic pyrophosphatase gene.

Using Inverse PCR to Identify the Entire Inorganic Pyrophosphatase (Gene from $T.$ $litoralis$ Gtenomic DNA The first step in using IPCR to amplify the entire $T.$ $litoralis$ PPase gene was to identify restriction enzymes that would cleave on either side of the $T.$ $litoralis$ inorganic pyrophosphatase gene. Fragments less than 2000 bp in size were desirable for best possible amplification. Southern blot analysis, as described in Example II.E., indicated four possible candidate restriction enzymes with six-base cleavage sites that would produce DNA fragments in the desired size range: BamHI (approximately 1600 bp), Eco RI (approximately 1800 bp), HindIII (approximately 870, 1500 bp) and Sac I (approximately 1300 bp). However, restriction enzymes with four-base cleavage sites are generally preferred for IPCR because they are more likely to cleave at an acceptable point within the flanking target sequence. Bfa I, Hae III, Hha I and Sau 3AI were selected because they do not cleave within the known 265 bp fragment. See Example II.D.. Each restriction digest contained 10 μg of $T.$ $litoralis$ genomic DNA in a total reaction volume of 400 μl. Each restriction enzyme (all from New England Biolabs, Inc.; Beverly, Mass.) was used in its recommended reaction buffer, to which 160–500 units of enzyme was added as follows: 400 units Bam HI, 400 units Eco RI, 400 units Hind III, 400 units Sac I, 200 units Bfa I, 500 units Hae III, 400 units Hha I and 160 units Sau 3AI. The mixtures were incubated at 37° C. for 6 hours. The digests were phenol/chloroform extracted and ethanol precipitated. Each DNA pellet was resuspended in 400 μl of ligase buffer (50 mM Tris-HCl, pH 7.8, 10 mM $MgCl_2$, 10 mM DTF, 1 mM ATP, 25 μg/ml BSA), then 5 μl T4 DNA ligase (NEB No. 202C) was added. The ligation was allowed to proceed at 16° C. overnight with the hope of forming monomeric circles. The ligase was heat killed for 20 minutes at 65° C. The ligation reactions were phenol/chloroform extracted and ethanol precipitated; each pellet was resuspended in 50 μl 1× TE (1× TE=10 mM Tris, 1 mM EDTA, pH 8.0).

Figure 4:
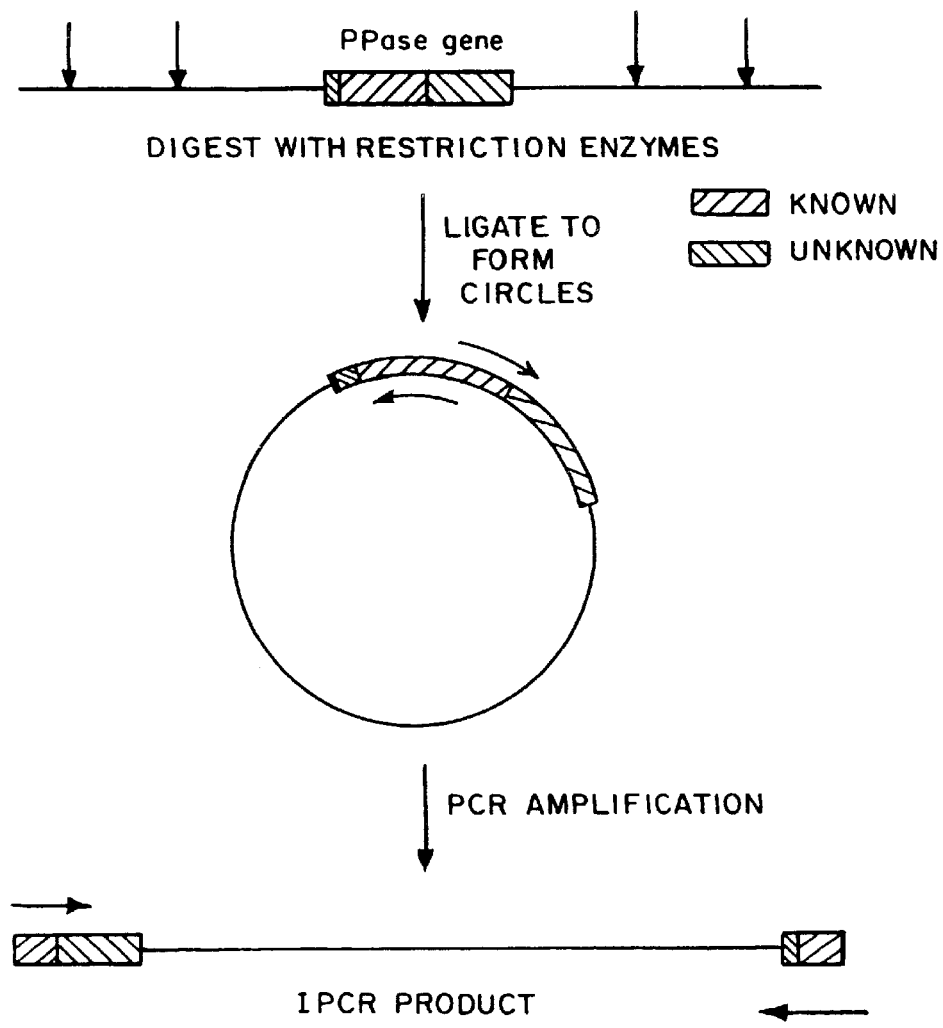
FIG. 4—is a flow chart diagram illustrating the steps involved in using inverse polymerase chain reaction (hereinafter "IPCR") to amplify the entire inorganic pyrophosphatase gene from *T. litoralis* genomic DNA, see Example II.E.. The known DNA sequence (265 bp) is shaded solid black while the unknown flanking sequences of interest are shaded a lighter color. Arrows directly over or under the region of known sequence, represents oligonucleotide primning sites used to amplify the unknown region.

The primers used for IPCR were derived from the 265 bp PCR fragment of the N-terminal half of the PPase gene. The sequence of the clockwise 24-mer is as follows: 5' GGTAC- GATGATGACGACCCGTTTG 3' (primer 120–96) (SEQ ID NO: 18). The sequence of the counterclockwise primer is: 5' GGATGATTCCATA GTCGACCGGG 3' (primer 120–95) (SEQ ID NO:19). Each IPCR reaction was set up as follows: 10 μl of circularized template from the ligation reactions, 200 μM dNTPs, 100 ng primers, 2.5 units AmpliTaq® DNA polymerase (Applied BioSystems Division, Perkin-Elmer Corporation; Foster City, Calif.) in PCR buffer ( 50 mM KCl, 10 mM Tris-HCl, pH 9.0 @ 25° C., 0.1% Triton X-100, 2.5 mM $MgCl_2$). Thirty cycles of denaturing at 95° C. for one minute, annealing at 50° C. for 2 minutes, and extending at 72° C. for 2 minutes were run in a thermal cycler. IPCR products were obtained from the following circularized templates: Bam HI (approximately 1600 bp), Hind III (approximately 1500 bp), Sac I (approximately 300 bp), Bfa I (approximately 1800 bp) and Sau 3AI (approximately 975 bp). The size of the IPCR products from the Bam HI and Hind III ligated circles agreed with the results obtained from the Southern blot analysis; the IPCR product from the Sac I ligated circle indicated the possibility of two internal Sac I sites due to its 300 bp size. No IPCR products were obtained at annealing temperature of 55° C. and 60° C. Attempts to obtain IPCR products from Eco RI, Hae III and Hha I digests were unsuccessful. Each IPCR product was purified using a Centricon-100 (Amicon; Danvers, Mass.) according to manufacturer's recommendations. See FIG. 4 for a flow chart illustrating the IPCR process used to obtain the entire inorganic pyrophosphatase gene from T. Iitoralis genomic DNA.

All the IPCR fragments were sequenced on a thermal cycler using the two IPCR primers (120–95 and 120–96), described above. All reactions were sequenced according to standard Applied BioSystems Division, Perkin-Elmer Corporation (Foster City, Calif.) Taq DyeDeoxy™ Teminator Cycle Sequencing Kit protocols. Sequencing reaction were set up as follows: 9.5 4l reaction pre-mix (16 μl 5× TACS Buffer, 4 μl dNTP Mix, 4 μl each of DyeDeoxy™ Terminators (A, G, C and T) and 2 μl AmpliTaq® DNA Polymerase), purified IPCR fragments (50–200 ng) and 3.2 pmol primer in a reaction volume of 20 μl. The sequencing reactions were cycled under the following conditions: preheat cycler to 95° C. for 5 minutes, 25 cycles of 1 minute denaturing at 95° C., 2 minutes annealing at 35° C. and 1 minute extension at 72° C. Extension products were purified using Centri-Sep (Princeton Separation Sciences; Princeton, N.J.) column purification protocol. Samples were run on an Applied BioSystems Division, Perkin-Elmer Corporation (Foster City, Calif.) Automated 373A DNA Sequencer. Data was analyzed using the Applied BioSystem Division, Perkin-Elmer Corporation (Foster City, Calif.) MacAssembler Programs (Factura™ and AutoAssembler™).

Four additional primers were designed from the DNA sequencing data obtained above. Two primers were designed from the Hind III/IPCR product: 5' GTTGAGGGCTGGTCAAAACGC 3' (primer 1078) (21-mer) (SEQ ID NO:20), and 5' GCGTTTTGACCAGCCCTCAAC 3' (primer 1079) (21-mer) (SEQ ID NO:21); and two primers were designed from the Bam HI/IPCR product: 5' GAGATTGTGCACTTCTTCCAGAGA 3' (primer 1080) (24-mer) (SEQ ID NO:22), 5' TCTCTGGAAGAAGTGCACAATCTC 3' (primer 1090) (24-mer) (SEQ ID NO:23). The IPCR products from the Bam HI, Hind III, Bfa I and Sau 3AI ligated circles were sequenced as described above with primers 1078, 1079, 1080 and 1090. The data was analyzed as described above.

The consensus sequence of the IPCR-generated fragments revealed the entire T. litoralis inorganic pyrophosphatase gene plus flanking DNA sequences both up- and downstream from the PPase gene. The corresponding amino acid sequence was compared to the amino acid sequences of other known pyrophosphatases (S. cerevisiae, A. thaliana, E. coli, PS-3 and T. acidophilum). It was confirmed that the entire PPase gene had been synthesized using IPCR, however, the gene was now divided into two pieces, in opposite orientations, on opposite ends of the IPCR-generated fragments.

EXAMPLE III

A. Over-Expression of the Thermnococcus Litoralis Inorganic Pyrophosphatase

The gene fragments obtained through methods in Example II may be used in a number of approaches, or combinations thereof, to obtain maximum expression of the cloned T. litoralis inorganic pyrophosphatase.

One such approach comprises separating the T. litoralis inorganic pyrophosphatase gene from its endogenous control elements and then operably linking the polymerase gene to a very tightly controlled promoter such as a T7 expression vector (Rosenberg, et al., Gene (1987) 56:125–135, the disclosure of which is hereby incorporated by reference herein). Insertion of the strong promoter may be accomplished by identifying convenient restriction targets near both ends of the T. litoralis inorganic pyrophosphatase gene and compatible restriction targets on the vector near the promoter, or generating restriction targets using site directed mutagenesis (Kunkel, Methods in Enzymology (1987) 154:367, the disclosure of which is hereby incorporated by reference herein) and transferring the T. litoralis inorganic pyrophosphatase gene into the vector in such an orientation as to be under transcriptional and translational control of the strong promoter.

T. litoralis inorganic pyrophosphatase may also be over-expressed by utilizing a strong ribosome binding site placed upstream of the T. litoralis inorganic pyrophosphatase gene to increase expression of the gene. See, Shine and Dalgarno, Proc. Natl. Acad. Sci. USA (1974) 71:1342–1346, the disclosure of which is hereby incorporated by reference herein.

Another approach for increasing expression of the T. litoralis inorganic pyrophosphatase comprises altering the DNA sequence of the gene by site directed mutagenesis or resynthesis to contain initiation codons that are more efficiently utilized than E. coli.

A further approach for increasing the expression of T. litoralis inorganic pyrophosphatase gene comprises designing oligonucleotide primers for hybridization to both sides of the T. litoralis inorganic pyrophosphatase gene; polymerase chain reaction can then be used to amplify the inorganic pyrophosphatase gene with engineered cloning sites on each end. The amplified fragment is inserted into one of the above-mentioned expression vectors such as pGW7 (ATCC No. 40166) or pET3A from William Studier, (Brookhaven, Nat. Lab., Upton, N.Y.). Both vectors contain a strong promoter and a ribosome binding site. Even strongly regulated promoters may be subject to read through expression, to limit this possibility transcription terminator sequences can be placed just upstream of the controlled promoter. Also, an inducible antisense promoter can be placed 3' to the end of the inorganic pyrophosphatase gene to reduce read through transcription.

Finally, T. litoralis inorganic pyrophosphatase may be more stable in eukaryotic systems like yeast or Baculovirus.

The T. litoralis inorganic pyrophosphatase may be produced from clones carrying the T. litoralis inorganic pyrophosphatase gene by propagation in a fermentor in a rich medium containing appropriate antibiotics. Cells are there-after harvested by centrifugation and disrupted by sonication to produce a crude cell extract containing the *T. litoralis* inorganic pyrophosphatase activity.

The crude extract containing the *T. litoralis* inorganic pyrophosphatase activity can be purified by the methods described in Example I, or by standard product purification techniques such as affinity-chromatography, or ion-exchange chromatography.

B. Using Primer Extension Reactions to Amplify the Entire *T. litoralis* Inorganic Pyrophosphatase Gene for Cloning and Over-Expression The consensus sequence from the IPCR-generated fragments was used to design new primers for the generation of primer extension products for cloning into an expression vector such as pMAL-cII, pAII17, pUC18 (all from New England Biolabs, Inc.; Beverly, Mass.). The following primers were designed at the N-terminus: (1) 5' P-ATGAATCCATTCCACGATTTAGAGCCT 3' (primer #1092) (SEQ ID NO:24), a 27-mer phosphorolyated at the 5'-end for blunt-end cloning into such vectors as pMAL-cII; (2) 5' GGGAATTC CATATGAATCCATTCCACGATTTAGAGCCT 3' (primer #1094) (SEQ ID NO:25), a 38-mer for cloning into an Nde I site in such vectors as pAII17 and (3) 5' CCG GAATTCATGAATCCATTCCACGATTRAGAGCCT 3' (primer #1093) (SEQ ID NO:26), a 36-mer for cloning into an Eco RI site in such vectors as pUC18. The following primer was designed at the C-terminus: 5' CGC GGATCCTCACTTCTTGAATTTCTCCTTGTAAAG 3' (primer #1095) (SEQ ID NO:27), a 33-mer for cloning into a Bam HI site. All four primers were separated and excised from a Novex 20% polyacrylamide TBE gel; the oligonucleotides were then purified for primer extension using SEP-PAK® C18 cartridges (Waters Corporation; Milford, Mass.).

The entire *T. litoralis* inorganic pyrophosphatase gene was synthesized for cloning using three different polymerase chain reactions with the following combination of primers: (1) 1092+1095, (2) 1093+1095 and (3) 1094+1095. A high fidelity thermophilic DNA polymerase with 3'→5' proofreading exonuclease activity (Vent$_R$® DNA polymerase (New England Biolabs, Inc.; Beverly, Mass.)) was used. In all three cases, the following reaction conditions were used. A 100 $\mu$l reaction contained 100 ng of genomic *T. litoralis* DNA, 1× ThemPol Buffer (10 mM KCl, 20 mM Tris-HCl (pH 8.8 @ 25° C.), 10 mM (NH$_4$)$_2$SO$_4$, 2 mM MgSO$_4$, 0.1% Triton X-100), additional 2 mM MgSO$_4$, 400 $\mu$M dNTP's, the primers (0.4 $\mu$M) and 1 unit of Vent$_R$® DNA polymerase. The primer extension reactions were run on a thermal cycler with a five minute preincubation step at 95° C. and 20 cycles of denaturing at 95° C. for one minute, annealing at 55° C. for one minute and extending at 72° C. for one minute. The primer extension reactions were purified using Centricon-100s (Amicon; Danvers, Mass.) according to manufacturer's recommendation. Final concentration of the purifed primer extension reactions were approximately 5 ng/$\mu$l in a 100 $\mu$l volume.

One reaction (1092+1095) was sequenced on a thermal cycler using the following primers: 1092 and 1095, described above, and primers 1080, 1090, 120–95 and 120–96, described in Example II.E.. All six reactions were sequenced according to standard Applied BioSystems Division, Perkin-Elmer Corporation (Foster City, Calif.) Taq Dyedeoxym Terminator Cycle Sequencing Kit protocols. Sequencing reactions were set up and data analyzed as previously described in Example II.D.. The concensus sequence revealed the expected complete DNA sequence of the *T. litoralis* inorganic pyrophosphatase, a 531 bp gene coding for a 176 amino acid (19,666 Da) subunit. See FIG. 5.

Restriction digests were performed on all three primer extension products. Each reaction contained 200 ng of the primer extension product in a total reaction volume of 50 $\mu$l. Each restriction enzyme (all from New England Biolabs Inc.; Beverly, Mass.) was used in conjuction with its recommended reaction buffer. Each reaction contained 10 units of each enzyme, and was incubated for 60 minutes at 37° C. The following digests were performed on the primer extension reactions: 1092+1095, Banm HI digest; 1093+1095, Eco RI/Bam HI double digest; and 1094+1095, Nde I/Bam HI double digest. The restriction enzymes were then heat-killed at 65° C. for 20 minutes; the reactions were phenol/chloroform extracted and ethanol precipitated. The resultant pellets were resuspended in 10 $\mu$l of 1× TE (1× TE=10 mM Tris, 1 mM EDTA, pH 8.0) for insertion into a suitable expression vector.

C. Cloning the Primer Extension Product into the Vector pAII17

One preferred mode of expressing the PPase gene is under the control of the T7 promotor system. Therefore, the appropriate primer extension product, as described in Example III.B., was cloned into the Nde I to Bam HI site on the vector pAll 17, a T7 vector based on pET11c. See Kong, et al., (1993) *Journal of Biological Chemistry*, 268:1965–1975. The primer extension reaction was ligated to pAII17 cut with Nde I/Bam HI as follows: 240 ng of the primer extension generated fragment was mixed with 48 to 72 ng of Nde I/Bam HI-cleaved and dephosphorolyated pAII17 (phenol/chloroformed, ethanol precipitated). The ligation reaction was performed in a volume of 40 $\mu$l in 1× ligation buffer (50 mM Tris, pH 7.5, 10 mM MgCl$_2$, 10 mM DTT, 0.5 mM ATP). T4 DNA ligase (1 $\mu$l) was added and the mixture was allowed to incubate at 16° C. for 16 hours. An aliquot of 20 $\mu$l was used to transform both *E. coli* strains ER 2497/pLysS and ER2497 respectively. After a 2-minute heat shock at 42° C., the cells were diluted with 100 $\mu$l of Luria-broth (L-broth) and grown for 20 minutes at 37° C. The transformed cell cultures were plated onto LB agar plates containing 100 $\mu$g/ml ampicillin. After overnight incubation at 37° C., the plates contained 16 colonies, 2 in the *E. coli* strain ER2497 and 14 in ER2497/pLysS.

To analyze the individual colonies, all 16 colonies from the above transformation were picked and plated on LB agar plates containing 100 $\mu$g/ml ampicillin. The 16 colonies were grown up in 10 ml cultures (L broth +100 $\mu$g/ml ampicillin) and the plasmids that they carried were prepared by the following miniprep purification procedure. Each culture was processed as follows: 3 ml of the overnight culture was pelleted at 12,000×g for 1–2 minutes in a microcentrifuge.

The supernatant was poured off and the cell pellet was resuspended in 200 $\mu$l of 50 mM Tris-HCl pH 7.5, 10 mM EDTA, 100 $\mu$g/ml RNase A. To lyse the cells, 200 $\mu$l of 0.2M NaOH, 1% SDS was added and mixed by inversion. After 5 minutes, 200 $\mu$l of 3M sodium acetate, pH 4.8, was added and mixed by inversion for an additional 5 minutes. The precipitate that formed was spun down at 12,000×g at 4° C. for 5 minutes. The supernatant was removed and added to 1 ml Celite (Fluka Chemika; Ronkonkoma; N.Y.) slurry (1.5 g Celite suspended in a solution of 66.84 g guanidine hydrochloride, 33.33 ml 3 M sodium acetate, pH 4.8, pH adjusted to 5.5 using 10M NaOH, final volume to 100 ml). The resin/DNA mix was packed into a minicolumn (Promega; Madison, Wis.); the resin was then dried by spinning at 12,000×g for 20 seconds in a microcentrifuge. The DNA was eluted by applying 50 $\mu$l of preheated (70° C.–80° C.) 10 mM Tris, 1 mM EDTA, pH 8.0, waiting one minute and then spinning at 12,000×g for 20 more seconds. The miniprepped DNA (5 μl) was subjected to digestion with Nde I/Bam HI. One clone (T7-5) appeared to have the appropriate size insert for the PPase gene.

To check for PPase expression and confirm the presence of the correct insert, 5 ml cultures (LB/Amp) of 4 colonies were grown, one being #T7-5. A 1 ml sample was removed when the cultures reached a density of $2 \times 10^8$ cells/ml ($A_{600}$ of ~0.5); each sample was microcentrifuged for 2 minutes, supernatant discarded and cells resuspended in 50 μl protein gel SDS-PAGE sample buffer (New England Biolabs, Inc.; Beverly, Mass., Product No. 7707). IPTG was added to the remaining cultures to 0.3 mM and incubated at 37° C. with good aeration for 2 hours. A 0.5 μl sample was removed, microcentrifuged for 2 minutes, supernatant discarded and cells resuspended in 100 μl of SDS-PAGE sample buffer. The samples were heated in a boiling water bath for 5 minutes and then electrophoresed (15 μl) on a 10% SDS-PAGE gel along with a set of protein molecular weight standards: MBP-p-galactosidase, 175 kDa; MBP-paramyosin, 83 kDa; glutamic dehydrogenase, 62 kDa; aldolase, 47.5 kDa; triosephosphate isomerase, 32.5 kDa; β-lactoglublin A, 25 kDa; lysozyme, 16.5 kDa; and aprotinin, 6.5 kDa. After staining the gel with ISS Pro-Blue (Integrated Separation Systems; Natick, Mass.), a large protein band was visible in the induced sample from #7-5; the size of the induced protein corresponded to the expected molecular weight of 20–21 kDa for the *T. litoralis* inorganic pyrophosphatase.

Figure 6:
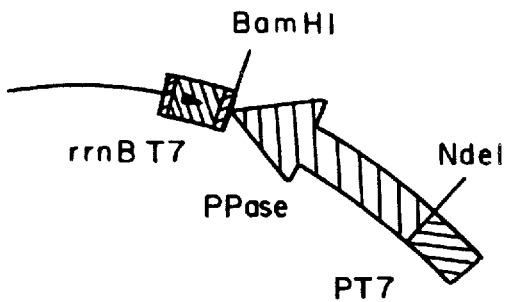
FIG. 6—is a schematic map of pAII17/PPase, a plasmid that encodes for the extremely thermostable *T. litoralis* inorganic pyrophosphatase of Example III.C.

The pAII17/PPase clone (T7-5) was subjected to DNA sequencing to confirm the correct construct. Plasmid DNA from T7-5 was isolated using standard procedures for cesium chloride/ethidium bromide purification. See Sambrook, Fritsch, and Maniatis, supra. T7-5 DNA was sequenced on a thermal cycler using the following primers: T7 universal primer #1248 (New England Biolabs, Inc.; Beverly, Mass.); primers 1092 and 1095, described in Example III.B.; and primers 1080, 1090, 120–95 and 120–96, described in Example HI.E.. All seven reactions were sequenced according to standard Applied BioSystems Division, Perkin-Elmer Corporation (Foster City, Calif.) Taq DyeDeoxy™ Terminator Cycle Sequencing Kit protocols. Sequencing reactions were set up and analyzed as described in Example II.D.. The DNA sequences revealed that the pAII17/PPase clone T7-5 had the correct *T. litoralis* inorganic pyrophosphatase promoter gene construct. See FIG. 6 for a diagram of the pAII17/PPase promoter construct.

Although the above-outlined steps represent the preferred mode for practicing the present invention, it will be apparent to those skilled in the art that the above-described approach can vary in accordance with techniques known in the art.

D. Cloning the Primer Extension Product into the Vector pUC18

Another preferred mode of expressing the PPase gene is in the pUC vector series, such as pUC18, a small, high copy number *E. coli* plasrmid cloning vector. The appropriate primer extension product, as described in Example III.B., was cloned into the Eco RI to Bam HI site. The primer extension reaction was ligated to pUC18 cut with Eco RI /Bam HI as follows: 160 ng-240 ng of the primer extension generated fragment was mixed with 50 ng of Eco RI/Bam HI-cleaved and dephosphorolyated pUC18 (phenol/chloroformed, ethanol precipitated). Two ligation reactions was performed containing either 2 μl or 3 μl of primer extension generated fragment, each in a volume of 20 μl in 1× ligation buffer (50 mM Tris, pH 7.5, 10 mM MgCl$_2$, 10 mM DTT, 0.5 mM ATP). T4 DNA ligase (New England Biolabs, Inc.; Beverly, Mass.) (0.5 μl) was added and the mixtures were allowed to incubate at 16° C. for 16 hours. CaCl competent cells (25 μl) of *E. coli* strain ER2426 were transformed with the ligation mixtures (Sambrook, Fritsch and Maniatis, supra, the disclosure of which is hereby incorporated by reference herein). The transformed cell cultures were plated onto LB agar plates containing 100 μg/ml ampicillin and incubated overnight at 37° C.

To analyze the individual colonies, 44 colonies from the above transformations were picked and plated on LB agar plates containing ampicillin. 36 colonies were grown up in 10 ml cultures of LB containing ampicillin (100 μg/ml) and kanamycin (50 μg/ml). The plasmids that they carried were prepared using a PEG modified mini alkalineprocessed asrecipitation procedure. Each culture was processed as follows: 4.5 ml of the overnight culture was pelleted at 12,000×g for 1–2 minutes in a microcentrifuge. The supernatant was poured off and the cell pellet was resuspended in 200 1μl of GTE buffer (50 mM glucose, 25 mM Tris-HCI pH 8.0, 10 mM EDTA). To lyse the cells, 300 μl of freshly prepared 0.2N NaOH, 1% SDS was added and mixed by inversion. After 5 minutes, 300 μl of 3M sodium acetate, pH 4.8, was added and mixed by inversion for an additional 5 minutes. The precipitate that formed was spun down at 12,000×g at 25° C. for 10 minutes. The supernatant was removed, RNase A was added to a final concentration of 20 μg/ml and incubated at 37° C. for 20 minutes. After RNase A treatment, the supernatant was extracted twice with 400 μl of chloroform and ethanol precipitated. The pellet was resuspended in 32 μl dH$_2$O, and precipitated with 8.0 μl 4M NaCl and 40 μl of autoclaved 13% PEG$_{8000}$ on ice for 20 minutes. The plasmid DNA was pelleted by centrifugation for 15 minutes at 4° C. and rinsed with 70% ethanol. The final pellet was resuspended in 20 μl dH$_2$O . The resultant DNA (2 μl) was subjected to digestion with Eco RI/Bam HI. Transformants that appear to have the proper construct for the *T. litoralis* PPase gene are pUC18/PPase clones 2, 4, 5, 6, 9, 10, 13, 19, 21, 28, 31 and 32.

Figure 7:
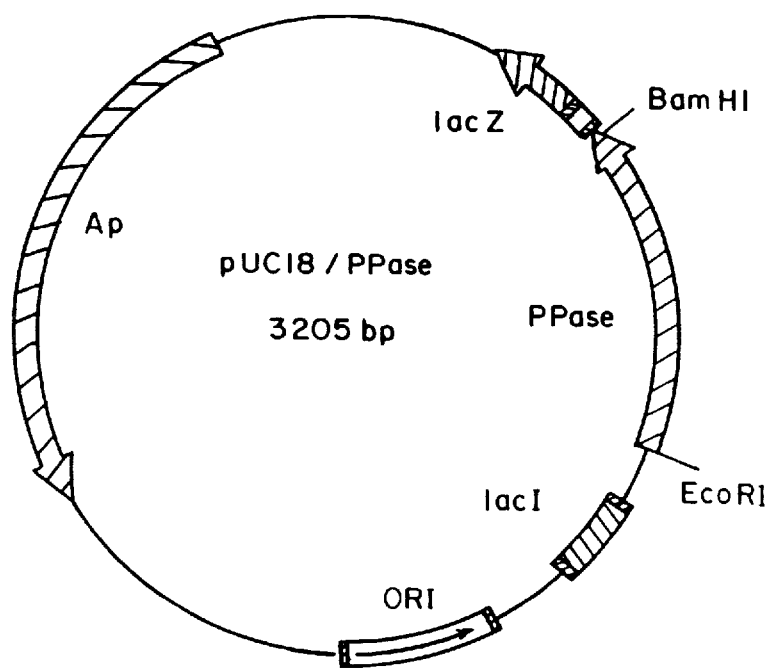
FIG. 7—is a schematic map of pUC 18/PPase, a plasmid that encodes for the extremely thermostable *T. litoralis* inorganic pyrophosphatase of Example III.D.

To confirm the presence of the correct insert, plasmid DNA from pUC18/PPase clones 2, 4, 5 and 6 were sequenced on a thermal cycler using the following primers: m13/pUC sequencing primer #1224 and M13/pUC reverse sequencing primer #1233 (both from New England Biolabs, Inc.; Beverly, Mass.). All eight reactions were sequenced according to standard Applied BioSystems Division, Perkin-Elmer Corporation (Foster City, Calif.) Taq DyeDeoxy™ Terminator Cycle Sequencing Kit protocols. Sequencing reactions were set up and analyzed as described in Example II.D. The DNA sequences revealed that all four pUC18/PPase clones (2, 4, 5, 6) have the correct PPase gene construct. See FIG. 7 for a diagram of the pUC18/PPase construct.

EXAMPLE IV

Purification of Recombinant *T. litoralis* Inorganic Pyrophosphatase

One preferred method for isolation and purification of recombinant *T. iitoralis* inorganic pyrophosphatase is accomplished using the multi-step process as follows:

*E. coli* strain ER 2497/pLysS containing the pAII17/PPase construct was grown up in 1 liter of Rich broth containing 100 μg/ml ampicillin at 37° C. in a shaking incubator. The cells were grown to a density of $2 \times 10^8$ cells/ml ($A_{600-0.5}$), (exponential growth phase) and induced with a final concentration of 0.3 mM IPTG for an additional 2 hours. The cells were harvested by centrifugation at 4000×g for 20 minutes, the supernatant was discarded and the cells were resuspended in 50 ml of buffer A (20 mM Tris, pH 7.5, 10 mM β-mercaptoethanol, and 0.1 mM EDTA) containing 50 mM NaCl. The resuspended cells (3 g) were then frozen overnight at −20° C.

The 3 g of cells obtained as described above, were sonicated at 4° C. The lysate was centrifuged at 14,000×g for 60 minutes at 4° C. The supernatant was heat treated for 15 minutes at 85° C. to denature the less thermostable *E. coli* host proteins, including the *E. coli* inorganic pyrophosphatase. After the heat treatment, the particulate material was removed by centrifugation at 5000×g for 10 minutes. The remaining supernatant contained approximately 40 mg of soluble protein, or approximately 20.5% of the protein contained in the crude extract (196 mg).

The remaining supernatant was then filtered using a Nalgene® (Rochester, N.Y.) disposable filter (0.2 μm) before applying it to a 5 ml DEAE Sepharose FF column (Pharmacia; Piscataway, N.J.). The column was then washed with 25 ml of buffer A containing 50 mM NaCl. The column was eluted with a 50 ml gradient from 50 mM to 1M NaCl in buffer A. Fractions were tested for inorganic pyrophosphatase activity using the thin layer chromatography assay, as described previously. The active fractions, comprising a 21 ml volume containing 40 mg protein, was pooled and is ready for dialysis into a storage buffer such as 0.1M KCl, 20 mM Tris (pH 8.0), 0.1 mM EDTA, 1 mM dithiothreitol and 50% glycerol at −20° C.

Figure 8:
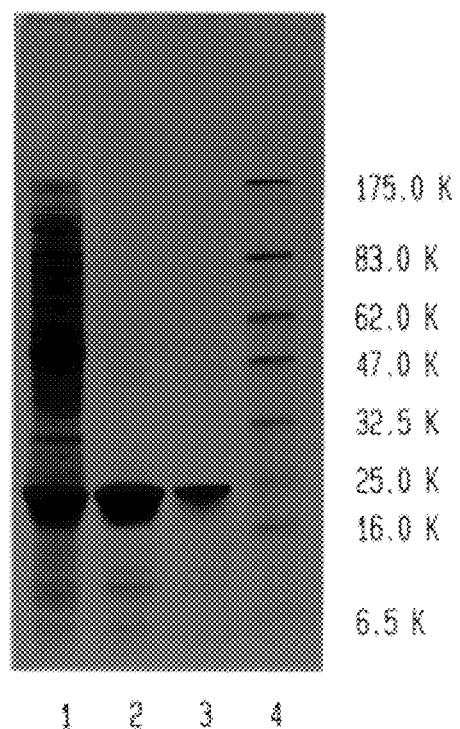
FIG. 8—is a photograph of the SDS-polyacrylamide gel of Example IV, showing the purification steps of the recombinant *T. litoralis* PPase. Lane 1, crude extract (2 hour induction); lane 2, after heat step at 85° C. for 15 minutes; lane 3, DEAE pool; and lane 4, prestained protein markers, broad range (New England Biolabs, Inc.; Beverly, Mass.), in order of decreasing molecular mass: MBP-β-galactosidase, MBP-paramyosin, glutamic dehydrogenase, aldolase, triose-phosphate isomerase, β-lactoglobulin A, lysozyme, aprotinin.

The *T. litoralis* inorganic pyrophosphatase obtained above was analyzed by SDS-polyacrylamide gel electrophoresis (10–20% SDS-PAGE) and subsequent staining of the proteins using a colloidal stain (ISS ProBlue; Integrated Separation Systems; Natick, Mass.). It was determined that the peak from the DEAE column was approximately 95% pure with one major band at 20–21 kDa, the same apparent molecular weight as the native *T. litoralis* inorganic pyrophosphatase. See FIG. 8. Moreover, the PPase obtained above had a specific activity of 1,750,000 NEB units/mg as determined by the thin layer chromatography assay in which one NEB unit is defined as the amount of enzyme that will convert 25 nmoles inorganic pyrophosphate at 75° C. in one hour in CircumVent™ buffer. Using the modifed Taussky and Schorr (Taussky and Schoor, supra, the disclosure of which is hereby incorporated by reference herein) assay, as previously described, a specific activity of 16,000–19,000 units/mg was determined in which one unit is defined as the amount of enzyme that will release 1.0 Amole orthophosphate per minute at 72° C. in a pH 9.0 Tris buffer.

The *T. litoralis* inorganic pyrophosphatase expressed from pAII17 and obtained through the above purification procedure was found to produce approximately 1200-fold the amount of enzyme (mg) per gram of cells when compared to the expression of the same enzyme when purified from *Thermococcus litoralis* strain NS-C (DSM NO. 5473) as in Example I.

Another preferred method for isolation and purification of recombinant *T. litoralis* inorganic pyrophosphatase is accomplished using *E. coli* strain ER2426 or similar *E. coli* strain containing the pUC18/PPase construct and by using a multistep process as follows:

*E. coli* strain ER2426 containing the pUC18/PPase construct was grown up in 1 liter of LB containing 100 μg/ml ampicillin and 50 μl/ml kanamycin at 37° C. in a shaking incubator. The cells were grown overnight to saturation (no IPTG induction). The cells were harvested by centrifugation at 4000×g for 20 minutes, the supernatant was discarded and the cells were resuspended in 50 ml of 50 mM NaCl, 20 mM Tris pH 7.5, 10 mM β-mercaptoethanol, and 0.1 mM EDTA. The resuspended cells (5.47 g) were then frozen at −20° C.

The 5.47 g of cells obtained as described above, were thawed and sonicated at 4° C. The lysate was centrifuged at 14,000×g for 60 minutes at 4° C. The supernatant was heat treated for 15 minutes at 85° C. to denature the less therrnostable *E. coli* host proteins and then centrifuged to remove the particulate material (5000×g for 10 minutes). The remaining supernatant was filtered using a Nalgene® (Rochester, N.Y.) disposable filter (0.2 μm). The remaining supernatant contained 23.7 mg of soluble protein, or approximately 5.7% of the protein contained in the crude extract (417.5 mg). The supernatant can be further purified by using ion-exchange column chromatography, such as DEAE Sepharose, or by using any such purification methods known in the art.

The *T. litoralis* inorganic pyrophosphatase obtained from ER2426 containing the pUC18/PPase construct was analyzed by SDS-polyacrylamide gel electrophoresis (10–20% SDS-PAGE) and subsequent staining of the proteins using a colloidal stain (ISS ProBlue; Integrated Separation Systems; Natick, Mass.); it was determined that the band at 20–21 kDa was the recombinant *T. litoralis* inorganic pyrophosphatase which agreed with the apparent molecular weight of the native *T. litoralis* inorganic pyrophosphatase. The *T. litoralis* inorganic pyrophosphatase expressed from pUC 18 and obtained through the above method was found to produce approximately 25-fold the amount of enzyme (mg) per gram of cells when compared to the expression of the same enzyme when purified from *ThermococciLs litoralis* strain NS-C (DSM NO. 5473) as in Example I.

EXAMPLE V

Extreme Thermostability of the *T. litoralis* Inorganic Pyrophosphatase

Figure 9:
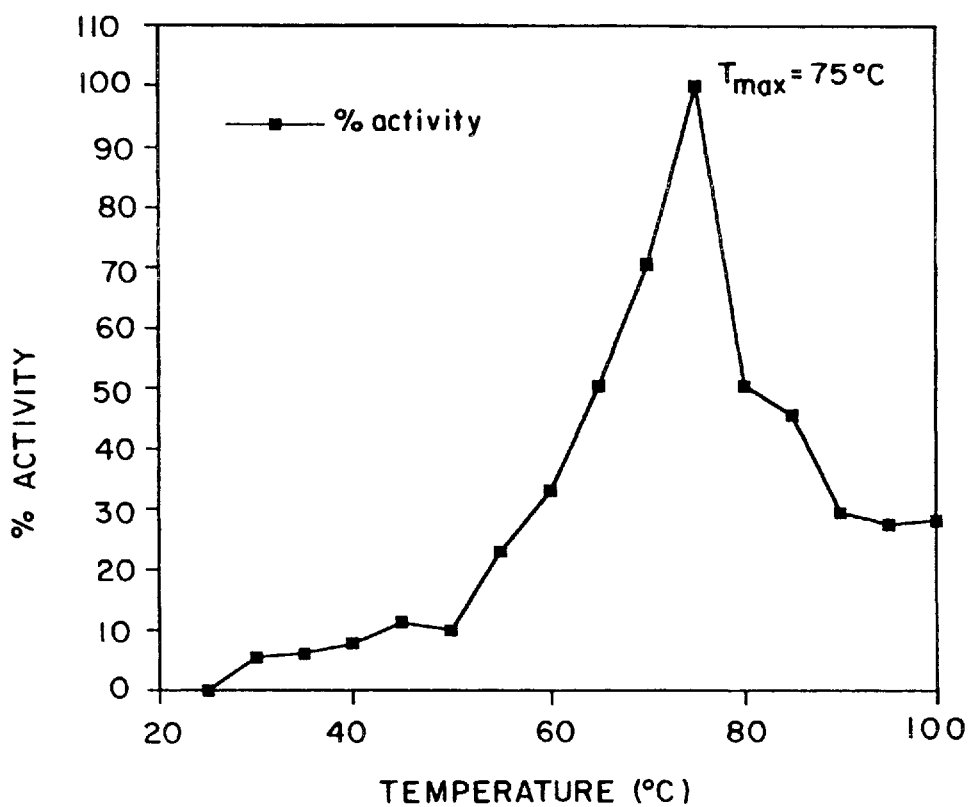
FIG. 9—is a graph showing the inorganic pyrophosphatase activity of Example V as it varies with temperature (25°–100° C.). Optimum temperature for the enzyme was approximately 75° C.

Temperature dependence of the PPase reaction is shown in FIG. 9. The maximum activity of the *T. litoralis* inorganic pyrophosphatase, purified by the method described in Example I, was determined to be at 75° C. Inorganic pyrophosphatase activity was measured using the modified method of Taussky and Schorr, supra, the disclosure of which is hereby incorporated by reference herein. The inorganic pyrophosphatase (one NEB unit) was incubated at 25° C. to 100° C. for 10 minutes in a 100 μl reaction containing 30 mM Tris pH 9.0, 1.5 mM $MgCl_2$ and 1.5 mM sodium pyrophosphate. The enzyme is then cooled quickly and complexed with 0.9 ml of Taussky-Schorr reagent (5.0 g ferrous sulfate, 10 ml 10% ammonium molybdate in 10 N sulfuric acid, in a final solution volume of 100 ml.) After 10 minutes, an absorbance reading is taken at 660 nm. Two samples were tested at each temperature.

The extreme thermostability of the *T. litoralis* inorganic pyrophosphatase purified as described in Example I was determined by the following method. Purified *T. litoralis* (approximately 1 NEB unit/10 μl) was preincubated in the absence of $Mg^{2+}$ at 100° C. in 50 mM Tris-HCl pH 9.0 buffer (total volume=150 μl). A 10 μl aliquots were removed at time zero and at 1, 2, 3, and 4 hours. Two reaction samples were measured at each time point. The inorganic pyrophosphatase activity was measured using the modified Taussky and Schorr, method as described above, supra.. 100% of the original pyrophosphatase activity was detected at 75° C. after incubation at 100° C. for 4 hours.

The heat stability of the *T. litoralis* inorganic pyrophosphatase is far more stable than the other commercially available inorganic pyrophosphatases. Commercially available PPases are heat resistant up to the following temperatures: *Escherichia coli* (80° C.) (Sigma; St. Louis, Mo.), Baker's yeast (50° C.) (Sigma, St. Louis, Mo.; Boehringer Mannheim, Indianapolis, Ind.; Amersham Corp, Arlington Heights, Ill.), *Bacillus stearothermophilus* (80° C.) (Sigma; St. Louis, Mo.). Heat resistance is defined as the temperature at which the activity of the enzyme decreases not more than 5% within 10 minutes. See Schreier, E. and Hohne, W. E., supra, the disclosure of which is hereby incorporated by reference herein.

Figure 10:
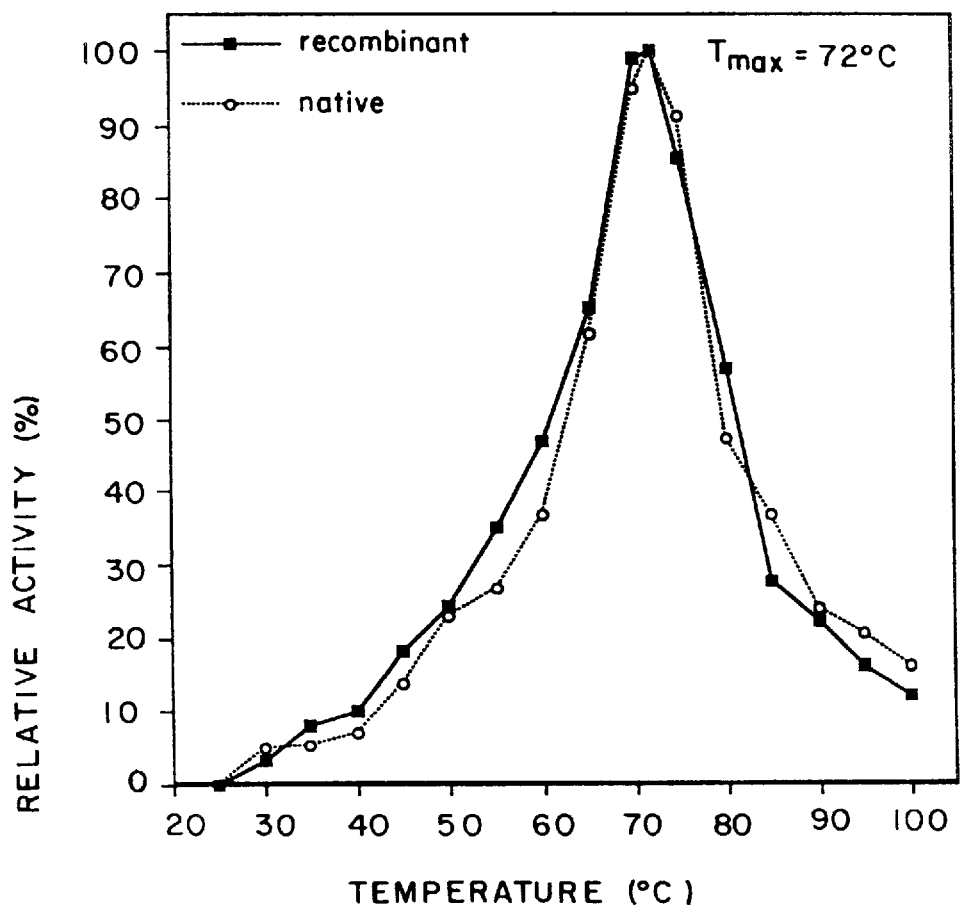
FIG. 10—is a graph showing the optimum temperature for pyrophosphatase activity for both the native and recombinant T. litoralis inorganic pyrophosphatases of Example V. PPase activity was tested between 25° C. and 100° C. Optimum temperature is more specifically 72° C., and not 75° C. as reported in FIG. 9.

The recombinant *T. litoralis* inorganic pyrophosphatase has the same extreme thermostability of the native enzyme. The native and recombinant *T. litoralis* PPases all maintain 100% of their original pyrophosphatase activity at 75° C. after incubation at 100° C. for 4 hours. Moreover, the temperature dependence of the PPase activity was redetermined as described above, using both the native and recombinant *T. litoralis* inorganic pyrophosphatases (from pAII17/PPase construct). The optimum temperature range for the *T. litoralis* PPase was analyzed more closely between 70° C. and 75° C.; it was determined that the optimum temperature was more specifically 72° C. and not 75° C. as previously determined. See FIG. 10.

EXAMPLE VI

Characterization of *T. litoralis* Inorganic Pyrophosphatase pH optimum

Figure 11:
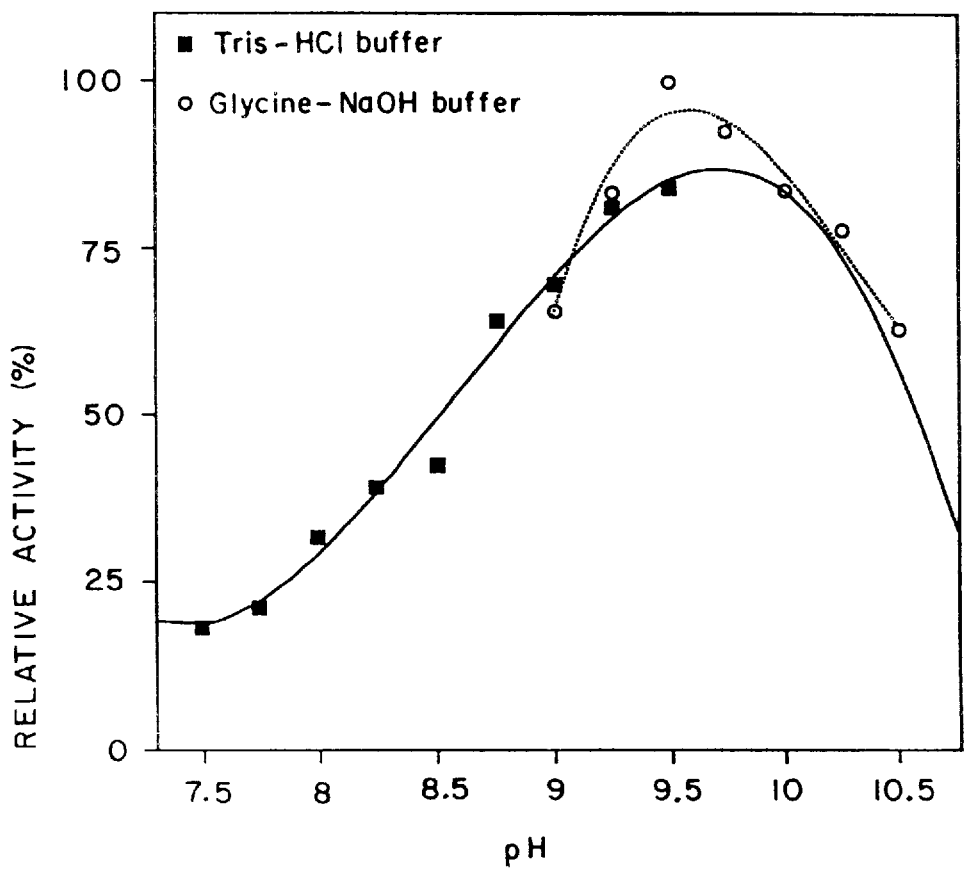
FIG. 11—is a graph showing the effect of varying pH on the activity of the T. litoralis PPase of Example VI. Activity was analyzed in both Tris-HCl (pH 7.5–9.5) and Glycine-NaOH (pH 9.0–10.5) buffers; optimum pH was 9.5 in both buffers, indicating that the T. litoralis PPase is an alkaline inorganic pyrophosphatase.

The activity of the *T. litoralis* inorganic pyrophosphatase was assayed using the modified Taussky-Schorr method as previously described, supra.. Various pH values were tested using both Tris-hydrocholoride (pH 7.5–9.5) and glycine-NaOH (pH 9.0–10.5) buffers, all at a final reaction concentration of 30 mM. When the *T. litoralis* PPase (1.3 ng) was assayed for 10 minutes at 72° C. in a reaction mixture (100 µl) containing 1.5 mM $MgCl_2$ and 1.5 mM $PP_i$, the enzyme exhibited a pH optimum of pH 9.5 in both Tris and glycine buffers. The glycine system provided better activity at a pH optimum of 9.5. See FIG. 11.

Molecular mass

Figure 12:
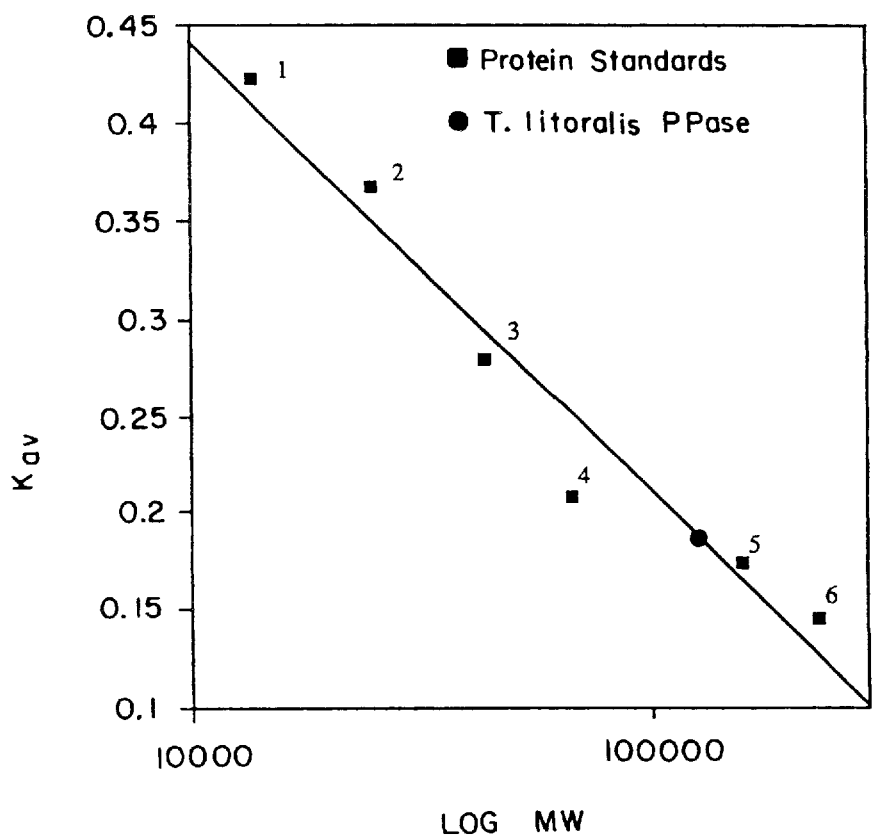
FIG. 12—is a graph of the molecular weight estimation of T. litoralis PPase by gel filtration on a Superose 12 HR 10/30 (Pharmacia; Piscataway, N.J.). The column was eluted with 50 mM Tris-HCl (pH 7.5) containing 100 mM NaCl buffer at a flow rate of 0.5 ml/min. Standards employed were as follows: (1) ribonuclease A, 13.7 kDa; (2) chymotrypsinogen, 25 kDa; (3) ovalbumin, 43 kDa; (4) bovine serum albumin, 67 kDa; (5) aldolase, 158 kDa; (6) catalase, 232 kDa.

The molecular mass of the *T. litoralis* inorganic pyrophosphatase was estimated by gel filtration in a Superose 12 HR 10/30 (Pharmacia; Piscataway, N.J.) (10×300 mm). The column was equilibrated with 50 mM Tris-HCl pH 7.5 containing 100 mM NaCl and run at a flow rate of 0.5 ml/min. The Superose 12 HR 10/30 had been previously calibrated with different standard proteins: Catalase (232 kDa), Aldolase (158 kDa), Bovine Serum Albumin (67 KDa), Ovalbumin (43 kDa), Chymotrypsinogen (25 kDa), and Ribonuclease A (13.7 kDa) (all from Pharmacia; Piscataway, N.J.). From the plot of log (molecular mass) versus the distribution coefficient (Kav), a value of 125 kDa was calculated for the molecular mass of *T. litoralis* inorganic pyrophosphatase. See FIG. 12. Since the apparent molecular mass of the monomer was determined to be 20 to 21 kDa on an SDS-PAGE and 19,666 Da by the DNA sequence, the enzyme is probably homohexameric. The homohexameric structure of the *Thermococcus litoralis* inorganic pyrophosphatase agrees with other known cytoplasmic PPases from eubacterial and archaeal sources which tend to be tetrameric or hexameric complexes with single subunits of 19 to 23 kDa.

Substrate specificity

The *T. litoralis* inorganic pyrophosphatase was highly specific for $PP_i$. Release of $P_i$ from $PPP_i$, $PPPP_i$ and dADP were 1.8%, 1.8% and 0.3% of that of $PP_i$, respectively. Hydrolysis of other substrates (pNPP, dATP, dAMP, dCTP, dGTP, dTTP) tested were negligible. The above substrates were tested at concentrations of 1.5 mM in a 100 µl reaction containing 30 mM Tris pH 9.0, 1.5 mM $MgCl_2$ and 1.3 ng PPase. The pyrophosphatase activity was detected after 10 minutes at 72° C. using the modified Taussky-Schorr assay method as previously described, supra.

TABLE I

Substrate specificity of inorganic pyrophosphatase from *T. litoralis*

| Cation | Percentage Activity |
|---|---|
| $PP_i$ | 100% |
| $PPP_i$ | 1.8% |
| $PPPP_i$ | 1.8% |
| pNPP | 0% |
| dATP | 0% |
| dADP | 0.3% |
| dAMP | 0% |
| dCTP | 0% |
| dGTP | 0% |
| dTTP | 0% |

Divalent cation specificity

The effect of various divalent cations on the catalytic activity of the enzyme was investigated. Magnesium provided the optimum activity; no activity was observed in the absence of divalent cations. Manganese, cobalt, zinc and nickel could be substituted, resulting in 4.6%, 2.8%, 0.9% and 0.6%, respectively, of the activity observed with magnesium. No activity was observed with calcium, copper or iron. The various divalent cations were tested at concentrations of 1.5 mM in a 100 µl reaction containing 30 mM Tris pH 9.0, 1.5 mM sodium pyrophosphate and 1.3 ng PPase. The pyrophosphatase activity was detected after 10 minutes at 72° C. using the modified Taussky-Schorr assay method as previously described, supra.

TABLE II

Effect of divalent cations on *T. litoralis* inorganic pyrophosphatase

| Cation | Percentage Activity |
|---|---|
| None | 0% |
| $Mg^{2+}$ | 100% |
| $Mn^{2+}$ | 4.6% |
| $Co^{2+}$ | 2.8% |
| $Zn^{2+}$ | 0.9% |
| $Ni^{2+}$ | 0.6% |
| $Ca^{2+}$ | 0% |
| $Cu^{2+}$ | 0% |
| $Fe^{2+}$ | 0% |

Effect of Pyrophosphate and Magnesium Concentrations on enzyme activity

Except at very high $Mg^{2+}$ concentrations, maximum enzyme activity occurred when the $Mg^{2+}$ to pyrophosphate ratio was 1:1. In the region of excess $PP_i$, inhibition was observed: excess $Mg^{2+}$ was also inhibitory.

The inorganic pyrophosphatase from *T. litoralis* did not appear to follow simple Michaelis-Menten kinetics when comparing reaction rates at different $PP_i$ and magnesium concentrations. However, if the initial velocities for low substrate concentrations of $PP_i$ and $Mg^{2+}$ and a $Mg^{2+}/PP_i$ ratio of one is used then the corresponding Lineweaver-Burke plot yields a straight line. The apparent $K_m$ value for the enzyme with respect to either $Mg^{2+}$ or $PP_i$ was calculated to be 1.0 mM.

Comparison of amino acid alignment to other known PPases

The complete amino acid sequence of the *T. litoralis* inorganic pyrophosphatase was compared to that of other known PPases. *T. litoralis* PPase exhibits similarity to the following known PPases: *T. acidophilum* (49%), thermophilic eubacterium PS-3 (49%), *S. acidocaldarius* (46%), *A. thaliana* (46%), *E. coli* (41%), *T. thermophilus* (39%), *S. cerevisiae* (27%). The similarity percentage is based on the percentage of identical residues with respect to the shorter of each sequence pair. All sequences were extracted from GENBANK, EMBL or SWISSPROT except for *S. acidocaldarius*. See Meyer, et. al. (1995), supra.

PROSITE document PDOC00325 lists an inorganic pyrophosphatase signature consensus pattern that is shared by ALL known sequences of this class as of Aug. 25, 1995:

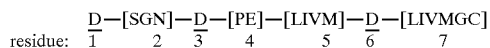

It is believed that the three aspartic acid residues (D, underlined) bind divalent metal cations. The inorganic pyrophosphatase from *Thermococcus litoralis* does not completely fit this pattern: instead the amino acid sequence for *T. litoralis* PPase in this region is:

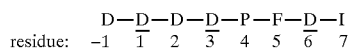

There are three changes to note when comparing the *T. litoralis* amino acid sequence to the inorganic pyrophosphatase signature concensus pattern found in PROSITE. First, there is an additional aspartic acid (D) preceding the concensus pattern which is not found in any of the other known PPase. Second, the amino acid residue in position 2 is an aspartic acid (D) and not serine (S), glycine (G) or asparagine (N). Third, the amino acid residue in position 5 is a phenylalanine (F) and not leucine (L), isoleucine (I), valine (V) or methionine (M). While all known pyrophosphatases have 3 aspartic acid (D) residues in this signature region to bind divalent cations, the inorganic pyrophosphatase from *T. litoralis* has an additional 2 aspartic acids to give a total of 5 aspartic acid residues in this signature region.

EXAMPLE VII

Performance of *T. litoralis* Inorganic Pyrophosphatase in DNA Sequencing

The performance of the thermostable inorganic pyrophosphatase of the present invention was examined in thermal cycle DNA sequencing reactions. The PPase from *T. litoralis* strain NS-C (DSM No. 5473), prepared as described in example I, was used in standard Applied BioSystems Division, Perkin-Elmer Corporation (Foster City, Calif.) Taq Dye Primer Cycle Sequencing. Two sequencing reactions were performed with and without the addition of PPase (1 NEB unit). Both reactions were sequenced according to standard Applied BioSystems Division, Perkin-Elmer Corporation (Foster City, Calif.) Taq Dye Primer Cycle Sequencing Kit protocols using M13mp18 templates and primer -21M13. The only change to the recommended protocol was that for the PPase reaction, one NEB (New England Biolabs, Inc.; Beverly, Mass.) unit of PPase was added to the diluted Taq reaction mix before the dye primer reactions were prepared. The two sequencing reactions were cycled under the following conditions: preheat cycler to 95° C. for 5 minutes, 15 cycles of 30 seconds denaturing at 95° C., 30 seconds annealing at 55° C. and 1 minute extension at 70° C. Extension products were purified using Centri-Sep spin columns (Princeton Separations, Inc.; Adelphia, N.J.). Samples were run on an Applied BioSystems Division, Perkin-Elmer Corporation (Foster City, Calif.) 373A DNA Sequencer. The DNA sequence traces show that the addition of *T. litoralis* PPase solves some sequencing artifacts present in the identical reaction performed without inclusion of the *T. litoralis* pyrophosphatase. See FIG. 13. The M13mp18 sequence without PPase shows dropout peaks at position 164 and position 310. When PPase is added to the reaction, these two peaks are resolved.

Figure 14A:
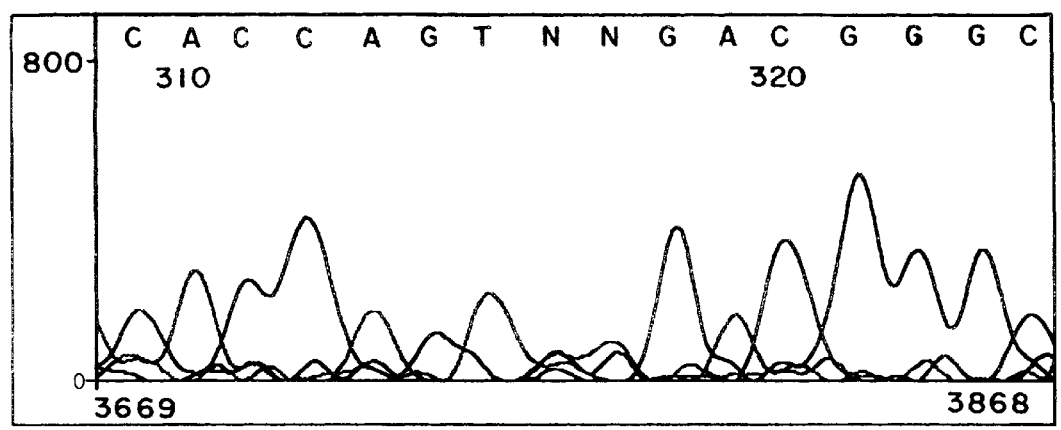
FIGS. 14A–14B—is the partial trace data from m13mp18 sequenced with AmpliTaq DNA polymerase (Applied BioSystems Division, Perkin-Elmer, Foster City, Calif.) with and without the addition of recombinant T. litoralis PPase of Example VII. The data shown in panel (FIG. 14A) (control-m13mp18, DyePrimer chemistry (–12mer), no PPase) was produced without the addition of PPase and contains missing G and A peaks at position 316 and 317 respectively. When the same m13mp18 template in panel (FIG. 14B) (+PPase-m13mp 18, DyePrimer chemistry (–21mer) - 2 NEB units PPase (recombinant)) is sequenced with the addition of PPase (2 NEB units), the peaks are resolved, here shown at position 310 and 311.
Figure 14B:
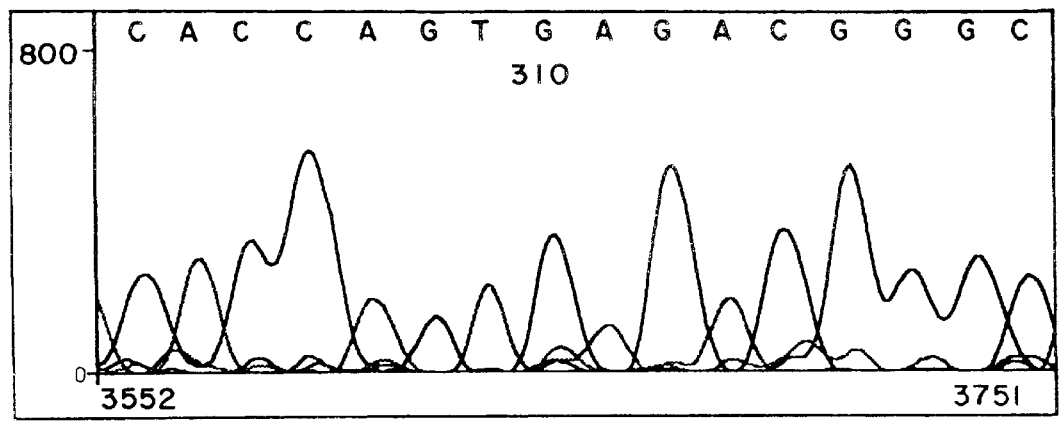
Figures 1, 13A:
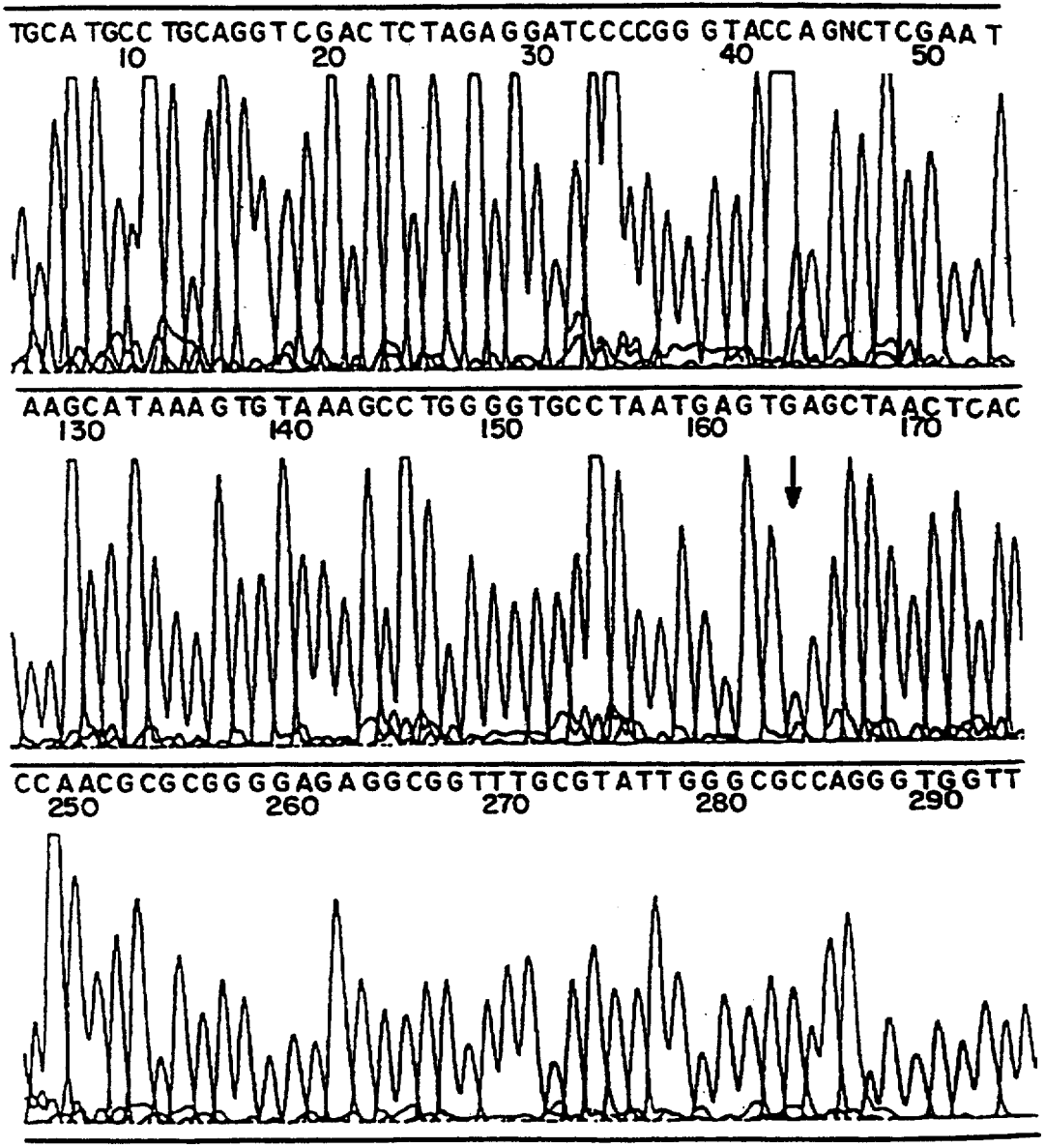
Figures 2, 13A:
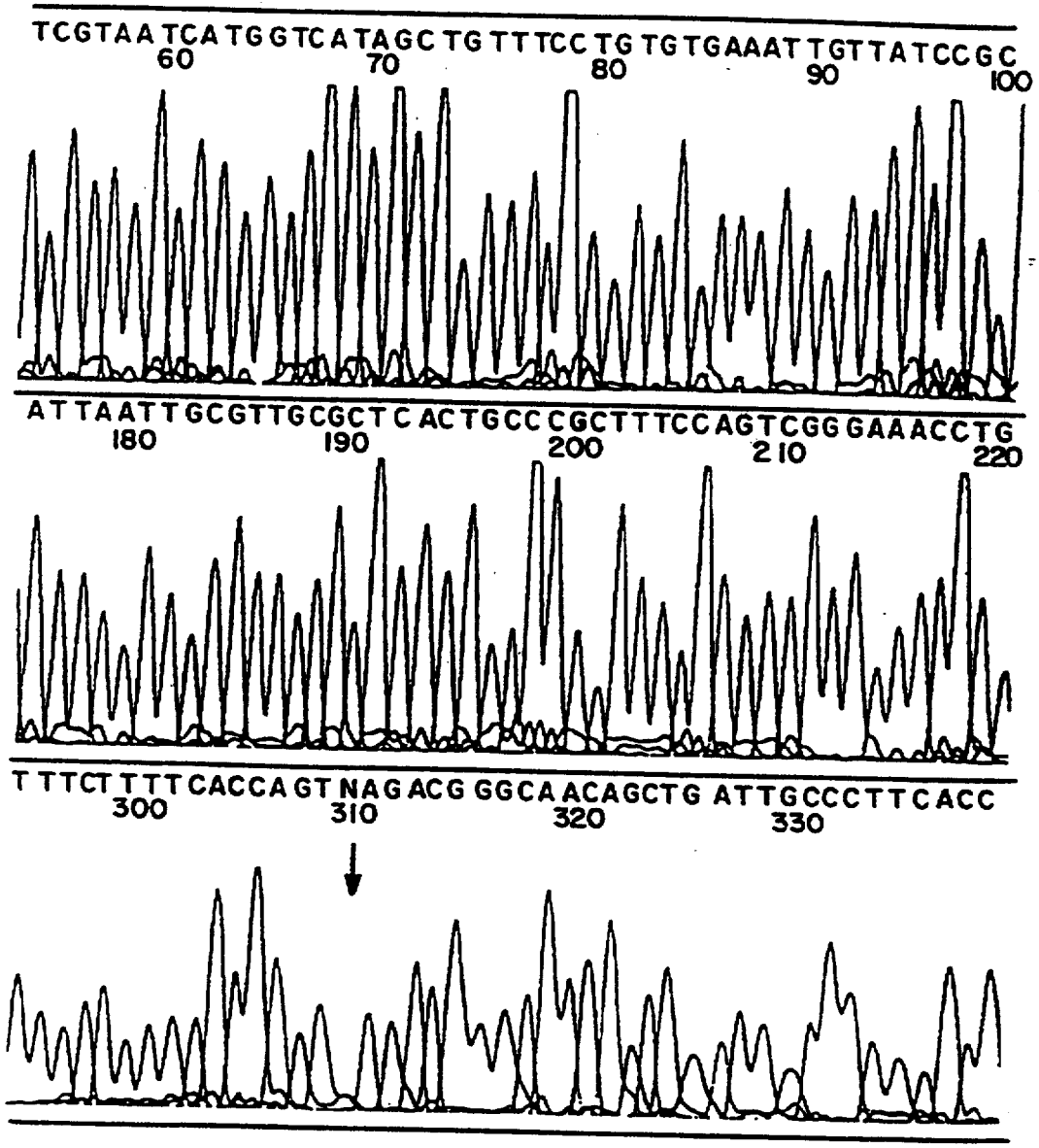

The recombinant *T. litoralis* PPase purified from *E. coli* strain ER2497/pLysS containing the pAII 17/PPase construct, prepared as described in example IV, was also examined in standard Applied BioSystems Division, Perkin-Elmer Corporation (Foster City, Calif.) Taq Dye Primer Cycle Sequencing. Sequencing reactions were set up exactly as described above. The DNA sequence traces show that the addition of *T. litoralis* PPase solves the problem of specific fragments disappearing on DNA sequencing gels. See FIG. 14. The m13mp18 sequence without PPase shows missing G and A peaks at position 316 and 317 respectively. When the same m 13mp18 template is sequence with the addition of PPase (2 NEB units), the peaks are resolved, here shown at position 310 and 311.

Missing sequencing peaks are thought to be due to pyrophosphorolysis, wherein the presence of excess inorganic pyrophosphate causes the hydrolysis of the 3'-terminal base. See generally, Deutsher et al., *J. Biol. Chem.* (1969) 244:3019 and Kornberg, *DNA Replication*, pp. 125–126, published by Freeman & Co., SF, the disclosure of which are hereby incorporated by reference herein. Inclusion of *T. litoralis* inorganic pyrophosphatase in a thermal cycle DNA sequencing reaction reduces the level of pyrophosphate and improves the uniformity of band intensity of nearby bands, thus improving reading of DNA sequencing gels.

The weak or missing fragments due to pyrophosphorolysis appears to be DNA sequence dependent, occurring at very specific sites. For example, the sequence dependence of the missing G peak in an m 13mp18 template using Applied BioSystems Division, Perkin-Elmer Corporation (Foster City, Calif.) Taq Dye Primer Cycle Sequencing is 5'-AGTGAG-3', where the underlined "G" disappears due to pyrophosphorolysis, but returns when *T. litoralis* PPase is added to the reaction.

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 222 base pairs
        ( B ) TYPE: nucleic acid
        ( C ) STRANDEDNESS: double -continued (D) TOPOLOGY: unknown (ii) MOLECULE TYPE: DNA (genomic)

(xi) SEQUENCE DESCRIPTION: SEQ ID NO:1:

| TTAGAGCCTG | GACCGGAAGT | ACCGGAAGTT | GTTTACGCCT | TAATAGAGAT | TCCAAAGGGG | 60 |
|---|---|---|---|---|---|---|
| AGCAGAAACA | AGTATGAGCT | TGACAAAAAG | ACCGGTCTTA | TAAAGCTCGA | TAGAGTTCTT | 120 |
| TACAGNCCAT | TCCACTACCC | GGTCGACTAT | GGAATCATCC | CACAAACATG | GTACGATGAT | 180 |
| GACGACCCGT | TTGACATCAT | GGTCATAATG | AGGGAGCCGA | CC | | 222 |

(2) INFORMATION FOR SEQ ID NO:2:

(i) SEQUENCE CHARACTERISTICS:
        (A) LENGTH: 74 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:2:

```
Leu Glu Pro Gly Pro Glu Val Pro Glu Val Val Tyr Ala Leu Ile Glu
 1               5                  10                  15
Ile Pro Lys Gly Ser Arg Asn Lys Tyr Glu Leu Asp Lys Lys Thr Gly
                20                  25                  30
Leu Ile Lys Leu Asp Arg Val Leu Tyr Ser Pro Phe His Tyr Pro Val
            35                  40                  45
Asp Tyr Gly Ile Ile Pro Gln Thr Trp Tyr Asp Asp Asp Pro Phe
50                      55                  60
Asp Ile Met Val Ile Met Arg Glu Pro Thr
65                      70
```

(2) INFORMATION FOR SEQ ID NO:3:

(i) SEQUENCE CHARACTERISTICS:
        (A) LENGTH: 286 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:3:

```
Thr Tyr Thr Thr Arg Gln Ile Gly Ala Lys Asn Thr Leu Glu Tyr Lys
 1               5                  10                  15
Val Tyr Ile Glu Lys Asp Gly Lys Pro Val Ser Ala Phe His Asp Ile
                20                  25                  30
Pro Leu Tyr Ala Asp Lys Glu Asn Asn Ile Phe Asn Met Val Val Glu
            35                  40                  45
Ile Pro Arg Trp Thr Asn Ala Lys Leu Glu Ile Thr Lys Glu Glu Thr
        50                  55                  60
Leu Asn Pro Ile Ile Gln Asp Thr Lys Lys Gly Lys Leu Arg Phe Val
65                      70                  75              80
Arg Asn Cys Phe Pro His His Gly Tyr Ile His Asn Tyr Gly Ala Phe
                    85              90                  95
Pro Gln Thr Trp Glu Asp Pro Asn Val Ser His Pro Glu Thr Lys Ala
                100                 105                 110
Val Gly Asp Asn Asp Pro Ile Asp Val Leu Glu Ile Gly Glu Thr Ile
            115                 120                 125
Ala Tyr Thr Gly Gln Val Lys Gln Val Lys Ala Leu Gly Ile Met Ala
```

|   |   |   |   |   |   |   |   |   |   |   |   |   |   |   |
|---|---|---|---|---|---|---|---|---|---|---|---|---|---|---|
|   |   |   | 130 |   |   |   |   | 135 |   |   |   | 140 |   |   |
| Leu 145 | Leu | Asp | Glu | Gly | Glu 150 | Thr | Asp | Trp | Lys | Val 155 | Ile | Ala | Ile | Asp 160 |
| Asn | Asp | Pro | Leu | Ala 165 | Pro | Lys | Leu | Asn | Asp 170 | Ile | Glu | Asp | Val | Glu 175 Lys |
| Tyr | Phe | Pro | Gly 180 | Leu | Leu | Arg | Ala | Thr 185 | Asn | Glu | Trp | Phe | Arg 190 | Ile Tyr |
| Lys | Ile | Pro 195 | Asp | Gly | Lys | Pro | Glu 200 | Asn | Gln | Phe | Ala | Phe 205 | Ser | Gly Glu |
| Ala | Lys 210 | Asn | Lys | Lys | Tyr | Ala 215 | Leu | Asp | Ile | Ile | Lys 220 | Glu | Thr | His Asp |
| Ser 225 | Trp | Lys | Gln | Leu | Ile 230 | Ala | Gly | Lys | Ser | Ser 235 | Asp | Ser | Lys | Gly Ile 240 |
| Asp | Leu | Thr | Asn | Val 245 | Thr | Leu | Pro | Asp | Thr 250 | Pro | Thr | Tyr | Ser | Lys 255 Ala |
| Ala | Ser | Asp | Ala 260 | Ile | Pro | Pro | Ala | Ser 265 | Leu | Lys | Ala | Asp | Ala 270 | Pro Ile |
| Asp | Lys | Ser 275 | Ile | Asp | Lys | Trp | Phe 280 | Phe | Ile | Ser | Gly | Ser 285 | Val |   |

( 2 ) INFORMATION FOR SEQ ID NO:4:

( i ) SEQUENCE CHARACTERISTICS:
        ( A ) LENGTH: 263 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:4:

|   |   |   |   |   |   |   |   |   |   |   |   |   |   |   |
|---|---|---|---|---|---|---|---|---|---|---|---|---|---|---|
| Met 1 | Ala | Glu | Ile | Lys 5 | Asp | Glu | Gly | Ser | Ala 10 | Lys | Gly | Tyr | Ala | Phe 15 Pro |
| Leu | Arg | Asn | Pro 20 | Asn | Val | Thr | Leu | Asn 25 | Glu | Arg | Asn | Phe | Ala 30 | Ala Phe |
| Thr | His | Arg 35 | Ser | Ala | Ala | Ala | His 40 | Pro | Trp | His | Asp | Leu 45 | Glu | Ile Gly |
| Pro | Glu 50 | Ala | Pro | Thr | Val | Phe 55 | Asn | Cys | Ala | Val | Glu 60 | Ile | Ser | Lys Gly |
| Gly 65 | Lys | Val | Lys | Tyr | Glu 70 | Leu | Asp | Lys | Asn | Ser 75 | Gly | Leu | Ile | Lys Val 80 |
| Asp | Arg | Val | Leu | Tyr 85 | Ser | Ser | Ile | Val | Tyr 90 | Pro | His | Asn | Tyr | Gly 95 Phe |
| Ile | Pro | Arg | Thr 100 | Ile | Cys | Glu | Asp | Ser 105 | Asp | Pro | Met | Asp | Val 110 | Leu Val |
| Leu | Met | Gln 115 | Glu | Pro | Val | Leu | Thr 120 | Gly | Ser | Phe | Leu | Arg 125 | Ala | Arg Ala |
| Ile | Gly 130 | Leu | Met | Pro | Met | Ile 135 | Asp | Gln | Gly | Glu | Lys 140 | Asp | Asp | Lys Ile |
| Ile 145 | Ala | Val | Cys | Ala | Asp 150 | Asp | Pro | Glu | Phe | Arg 155 | His | Tyr | Arg | Asp 160 Ile |
| Lys | Glu | Leu | Pro | Pro 165 | His | Arg | Leu | Ala | Glu 170 | Ile | Arg | Arg | Phe | Phe 175 Glu |
| Asp | Tyr | Lys | Lys 180 | Asn | Glu | Asn | Lys | Lys 185 | Val | Asp | Val | Glu | Ala 190 | Phe Leu |
| Pro | Ala | Gln 195 | Ala | Ala | Ile | Asp | Ala 200 | Ile | Lys | Asp | Ser | Met 205 | Asp | Leu Tyr |

```
Glu  Leu  Thr  Ser  Lys  Leu  Ala  Cys  Asn  Ala  Asn  Glu  Glu  Thr  Ser  Pro
     210            215                      220

Phe  Pro  Phe  Leu  Pro  Val  Cys  Leu  Asp  Ile  Thr  Glu  Ala  Ala  Phe  Tyr
225            230                      235                            240

Thr  Thr  Cys  Met  Leu  Asp  Lys  Ile  Ser  Ile  Gly  Ala  Phe  Asn  Phe  Val
               245                      250                      255

Met  Leu  Ile  Arg  Lys  His  Cys
               260
```

(2) INFORMATION FOR SEQ ID NO:5:

(i) SEQUENCE CHARACTERISTICS:
        (A) LENGTH: 175 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:5:

```
Ser  Leu  Leu  Asn  Val  Pro  Ala  Gly  Lys  Asp  Leu  Pro  Glu  Asp  Ile  Tyr
1              5                        10                            15

Val  Val  Ile  Glu  Ile  Pro  Ala  Asn  Ala  Asp  Pro  Ile  Lys  Tyr  Glu  Ile
               20                  25                        30

Asp  Lys  Glu  Ser  Gly  Ala  Leu  Phe  Val  Asp  Arg  Phe  Met  Ser  Thr  Ala
          35                       40                       45

Met  Phe  Tyr  Pro  Cys  Asn  Tyr  Gly  Tyr  Ile  Asn  His  Thr  Leu  Ser  Leu
     50                       55                       60

Asp  Gly  Asp  Pro  Val  Asp  Val  Leu  Val  Pro  Thr  Pro  Tyr  Pro  Leu  Gln
65                       70                  75                            80

Pro  Gly  Ser  Val  Ile  Arg  Cys  Arg  Pro  Val  Gly  Val  Leu  Lys  Met  Thr
               85                       90                       95

Asp  Glu  Ala  Gly  Glu  Asp  Ala  Lys  Leu  Val  Ala  Val  Pro  His  Ser  Lys
               100                      105                 110

Leu  Ser  Lys  Glu  Tyr  Asp  His  Ile  Lys  Asp  Val  Asn  Asp  Leu  Pro  Glu
          115                      120                 125

Leu  Leu  Lys  Ala  Gln  Ile  Ala  His  Phe  Phe  Glu  His  Tyr  Lys  Asp  Leu
     130                      135                 140

Glu  Lys  Gly  Lys  Trp  Val  Lys  Val  Glu  Gly  Trp  Glu  Asn  Ala  Glu  Ala
145                 150                      155                           160

Ala  Lys  Ala  Glu  Ile  Val  Ala  Ser  Phe  Glu  Arg  Ala  Lys  Asn  Lys
               165                      170                 175
```

(2) INFORMATION FOR SEQ ID NO:6:

(i) SEQUENCE CHARACTERISTICS:
        (A) LENGTH: 164 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:6:

```
Ala  Phe  Glu  Asn  Lys  Ile  Val  Glu  Ala  Phe  Ile  Glu  Ile  Pro  Thr  Gly
1              5                        10                            15

Ser  Gln  Asn  Lys  Tyr  Glu  Phe  Asp  Lys  Glu  Arg  Gly  Ile  Phe  Lys  Leu
               20                  25                        30

Asp  Arg  Val  Leu  Tyr  Ser  Pro  Met  Phe  Tyr  Pro  Ala  Glu  Tyr  Gly  Tyr
          35                       40                       45
```

Leu Gln Asn Thr Leu Ala Leu Asp Gly Asp Pro Leu Asp Ile Leu Val
    50              55              60

Ile Thr Thr Asn Pro Pro Phe Pro Gly Cys Val Ile Asp Thr Arg Val
65              70              75              80

Ile Gly Tyr Leu Asn Met Val Asp Ser Gly Glu Glu Asp Ala Lys Leu
            85              90              95

Ile Gly Val Pro Val Glu Asp Pro Arg Phe Asp Glu Val Arg Ser Ile
            100             105             110

Glu Asp Leu Pro Gln His Lys Leu Lys Glu Ile Ala His Phe Phe Glu
            115             120             125

Arg Tyr Lys Asp Leu Gln Gly Lys Arg Thr Glu Ile Gly Thr Trp Glu
        130             135             140

Gly Pro Glu Ala Ala Ala Lys Leu Ile Asp Glu Cys Ile Ala Arg Tyr
145             150             155             160

Asn Glu Gln Lys (2) INFORMATION FOR SEQ ID NO:7:

(i) SEQUENCE CHARACTERISTICS:
        (A) LENGTH: 179 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:7:

Met Glu Ser Phe Tyr His Ser Val Pro Val Gly Pro Lys Pro Pro Glu
1               5               10              15

Glu Val Tyr Val Ile Val Glu Ile Pro Arg Gly Ser Arg Val Lys Tyr
            20              25              30

Glu Ile Ala Lys Asp Phe Pro Gly Met Leu Val Asp Arg Val Leu Tyr
        35              40              45

Ser Ser Val Val Tyr Pro Val Asp Tyr Gly Leu Ile Pro Arg Thr Leu
    50              55              60

Tyr Tyr Asp Gly Asp Pro Met Asp Val Met Val Leu Ile Ser Gln Pro
65              70              75              80

Thr Phe Pro Gly Ala Ile Met Lys Val Arg Pro Ile Gly Met Met Lys
            85              90              95

Met Val Asp Gln Gly Glu Thr Asp Asn Lys Ile Leu Ala Val Phe Asp
            100             105             110

Lys Asp Pro Asn Val Ser Tyr Ile Lys Asp Leu Lys Asp Val Asn Ala
            115             120             125

His Leu Leu Asp Glu Ile Ala Asn Phe Phe Ser Thr Tyr Lys Ile Leu
    130             135             140

Glu Lys Lys Glu Thr Lys Val Leu Gly Trp Glu Gly Lys Glu Ala Ala
145             150             155             160

Leu Lys Glu Ile Glu Val Ser Ile Lys Met Tyr Glu Glu Lys Tyr Gly
            165             170             175

Lys Lys Asn (2) INFORMATION FOR SEQ ID NO:8:

(i) SEQUENCE CHARACTERISTICS:
        (A) LENGTH: 94 amino acids
        (B) TYPE: amino acid
        (C) STRANDEDNESS: unknown
        (D) TOPOLOGY: unknown ( i i ) MOLECULE TYPE: protein ( x i ) SEQUENCE DESCRIPTION: SEQ ID NO:8:

| Met | Asn | Pro | Phe | His | Asp | Leu | Glu | Pro | Gly | Pro | Glu | Val | Pro | Glu | Val |
|---|---|---|---|---|---|---|---|---|---|---|---|---|---|---|---|
| 1 | | | | 5 | | | | | 10 | | | | | 15 | |

| Val | Tyr | Ala | Leu | Ile | Glu | Ile | Pro | Lys | Gly | Ser | Arg | Asn | Lys | Tyr | Glu |
|---|---|---|---|---|---|---|---|---|---|---|---|---|---|---|---|
| | | | 20 | | | | | 25 | | | | | 30 | | |

| Leu | Asp | Lys | Lys | Thr | Gly | Leu | Ile | Lys | Leu | Asp | Arg | Val | Leu | Tyr | Ser |
|---|---|---|---|---|---|---|---|---|---|---|---|---|---|---|---|
| | | | 35 | | | | 40 | | | | | 45 | | | |

| Pro | Phe | His | Tyr | Pro | Val | Asp | Tyr | Gly | Ile | Ile | Pro | Gln | Thr | Trp | Tyr |
|---|---|---|---|---|---|---|---|---|---|---|---|---|---|---|---|
| | | 50 | | | | | 55 | | | | 60 | | | | |

| Asp | Asp | Asp | Asp | Pro | Phe | Asp | Ile | Met | Val | Ile | Met | Arg | Glu | Pro | Thr |
|---|---|---|---|---|---|---|---|---|---|---|---|---|---|---|---|
| 65 | | | | | 70 | | | | | 75 | | | | | 80 |

| Tyr | Pro | Gly | Val | Leu | Ile | Glu | Ala | Arg | Pro | Ile | Gly | Gly | Phe |
|---|---|---|---|---|---|---|---|---|---|---|---|---|---|
| | | | | 85 | | | | | 90 | | | | |

( 2 ) INFORMATION FOR SEQ ID NO:9:

( i ) SEQUENCE CHARACTERISTICS:
        ( A ) LENGTH: 531 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:9:

| ATGAATCCAT | TCCACGATTT | AGAGCCTGGA | CCGGAAGTAC | CGGAAGTTGT | TTACGCCTTA | 60 |
|---|---|---|---|---|---|---|
| ATAGAGATTC | CAAAGGGGAG | CAGAAACAAG | TATGAGCTTG | ACAAAAAGAC | CGGCCTTATA | 120 |
| AAGCTCGATA | GAGTTCTTTA | CAGCCCATTC | CACTACCCGG | TCGACTATGG | AATCATCCCA | 180 |
| CAAACATGGT | ACGATGATGA | CGACCCGTTT | GACATCATGG | TCATAATGAG | GGAGCCAACA | 240 |
| TATCCGGGAG | TTCTTATTGA | GGCAAGACCA | ATAGGCCTCT | TCAAGATGAT | AGACAGCGGC | 300 |
| GACAAGGACT | ACAAGGTATT | GGCAGTTCCA | GTGAAGATC | CCTACTTTAA | TGACTGGAAG | 360 |
| GACATAAGCG | ACGTTCCGAA | GGCTTTCCTT | GACGAGATTG | CGCACTTCTT | CCAGAGATAC | 420 |
| AAAGAGCTCC | AAGGTAAGGA | AATCATTGTT | GAGGGCTGGG | AAAACGCAGA | GAAGGCAAAG | 480 |
| CAAGAAATAC | TTAGGGCAAT | AGAACTTTAC | AAGGAGAAAT | TCAAGAAGTG A | | 531 |

( 2 ) INFORMATION FOR SEQ ID NO:10:

( i ) SEQUENCE CHARACTERISTICS:
        ( A ) LENGTH: 176 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met | Asn | Pro | Phe | His | Asp | Leu | Glu | Pro | Gly | Pro | Glu | Val | Pro | Glu | Val |
|---|---|---|---|---|---|---|---|---|---|---|---|---|---|---|---|
| 1 | | | | 5 | | | | | 10 | | | | | 15 | |

| Val | Tyr | Ala | Leu | Ile | Glu | Ile | Pro | Lys | Gly | Ser | Arg | Asn | Lys | Tyr | Glu |
|---|---|---|---|---|---|---|---|---|---|---|---|---|---|---|---|
| | | | 20 | | | | | 25 | | | | | 30 | | |

| Leu | Asp | Lys | Lys | Thr | Gly | Leu | Ile | Lys | Leu | Asp | Arg | Val | Leu | Tyr | Ser |
|---|---|---|---|---|---|---|---|---|---|---|---|---|---|---|---|
| | | | 35 | | | | 40 | | | | | 45 | | | |

| Pro | Phe | His | Tyr | Pro | Val | Asp | Tyr | Gly | Ile | Ile | Pro | Gln | Thr | Trp | Tyr |
|---|---|---|---|---|---|---|---|---|---|---|---|---|---|---|---|
| | | 50 | | | | | 55 | | | | 60 | | | | |

| Asp | Asp | Asp | Asp | Pro | Phe | Asp | Ile | Met | Val | Ile | Met | Arg | Glu | Pro | Thr |
|---|---|---|---|---|---|---|---|---|---|---|---|---|---|---|---|
| 65 | | | | | 70 | | | | | 75 | | | | | 80 |

| Tyr | Pro | Gly | Val | Leu<br>85 | Ile | Glu | Ala | Arg | Pro<br>90 | Ile | Gly | Leu | Phe | Lys<br>95 | Met |
|---|---|---|---|---|---|---|---|---|---|---|---|---|---|---|---|
| Ile | Asp | Ser | Gly<br>100 | Asp | Lys | Asp | Tyr | Lys<br>105 | Val | Leu | Ala | Val | Pro<br>110 | Val | Glu |
| Asp | Pro | Tyr<br>115 | Phe | Asn | Asp | Trp | Lys<br>120 | Asp | Ile | Ser | Asp | Val<br>125 | Pro | Lys | Ala |
| Phe | Leu<br>130 | Asp | Glu | Ile | Ala | His<br>135 | Phe | Phe | Gln | Arg | Tyr<br>140 | Lys | Glu | Leu | Gln |
| Gly<br>145 | Lys | Glu | Ile | Ile | Val<br>150 | Glu | Gly | Trp | Glu | Asn<br>155 | Ala | Glu | Lys | Ala | Lys<br>160 |
| Gln | Glu | Ile | Leu | Arg<br>165 | Ala | Ile | Glu | Leu | Tyr<br>170 | Lys | Glu | Lys | Phe | Lys<br>175 | Lys |

( 2 ) INFORMATION FOR SEQ ID NO:11:

( i ) SEQUENCE CHARACTERISTICS:
        ( A ) LENGTH: 37 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:11:

| Met<br>1 | Asn | Pro | Phe | His<br>5 | Asp | Leu | Glu | Pro | Gly<br>10 | Pro | Glu | Val | Pro | Glu<br>15 | Val |
|---|---|---|---|---|---|---|---|---|---|---|---|---|---|---|---|
| Val | Tyr | Ala | Leu<br>20 | Ile | Glu | Ile | Pro | Lys<br>25 | Gly | Ser | Arg | Asn | Lys<br>30 | Tyr | Glu |
| Leu | Asp | Lys | Lys | Thr<br>35 | | | | | | | | | | | |

( 2 ) INFORMATION FOR SEQ ID NO:12:

( i ) SEQUENCE CHARACTERISTICS:
        ( A ) LENGTH: 18 amino acids
        ( B ) TYPE: amino acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:12:

| Arg<br>1 | Glu | Pro | Thr | Tyr<br>5 | Pro | Gly | Val | Leu | Ile<br>10 | Glu | Ala | Arg | Pro | Ile<br>15 | Gly |
|---|---|---|---|---|---|---|---|---|---|---|---|---|---|---|---|
| Gly | Phe | | | | | | | | | | | | | | |

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY:
        ( B ) LOCATION: 6
        ( D ) OTHER INFORMATION: /note= "Y = C or T"

( i x ) FEATURE:
        ( A ) NAME/KEY:
        ( B ) LOCATION: 9
        ( D ) OTHER INFORMATION: /note= "N = C, T, A or G"

( i x ) FEATURE:
    ( A ) NAME/KEY:
    ( B ) LOCATION: 12
    ( D ) OTHER INFORMATION: /note= "Y = C or T"

( i x ) FEATURE:
    ( A ) NAME/KEY:
    ( B ) LOCATION: 15
    ( D ) OTHER INFORMATION: /note= "Y = C or T"

( x i ) SEQUENCE DESCRIPTION: SEQ ID NO:13:

ATGAAYCCNT TYCAYGA                                                                           17

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY:
        ( B ) LOCATION: 3
        ( D ) OTHER INFORMATION: /note= "H = A, C or T"

( i x ) FEATURE:
        ( A ) NAME/KEY:
        ( B ) LOCATION: 6
        ( D ) OTHER INFORMATION: /note= "R = A or G"

( i x ) FEATURE:
        ( A ) NAME/KEY:
        ( B ) LOCATION: 9
        ( D ) OTHER INFORMATION: /note= "H = A, C or T"

( i x ) FEATURE:
        ( A ) NAME/KEY:
        ( B ) LOCATION: 12
        ( D ) OTHER INFORMATION: /note= "N = C, T, A or G"

( i x ) FEATURE:
        ( A ) NAME/KEY:
        ( B ) LOCATION: 15
        ( D ) OTHER INFORMATION: /note= "R = A or G"

( x i ) SEQUENCE DESCRIPTION: SEQ ID NO:14:

ATHGARATHC CNAARGG                                                                    17

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY:
        ( B ) LOCATION: 3
        ( D ) OTHER INFORMATION: /note= "N = C, T, A or G"

( i x ) FEATURE:
        ( A ) NAME/KEY:
        ( B ) LOCATION: 6
        ( D ) OTHER INFORMATION: /note= "N = C, T, A or G"

( i x ) FEATURE:
        ( A ) NAME/KEY:
        ( B ) LOCATION: 9
        ( D ) OTHER INFORMATION: /note= "N = C, T, A or G"

( i x ) FEATURE:
    ( A ) NAME/KEY:
    ( B ) LOCATION: 12
    ( D ) OTHER INFORMATION: /note= "R = A or G"

( i x ) FEATURE:
    ( A ) NAME/KEY:
    ( B ) LOCATION: 15
    ( D ) OTHER INFORMATION: /note= "N = C, T, A or G"

( i x ) FEATURE:
    ( A ) NAME/KEY:
    ( B ) LOCATION: 18
    ( D ) OTHER INFORMATION: /note= "N = C, T, A or G"

( i x ) FEATURE:
    ( A ) NAME/KEY:
    ( B ) LOCATION: 21
    ( D ) OTHER INFORMATION: /note= "Y = C or T"

( x i ) SEQUENCE DESCRIPTION: SEQ ID NO:15:

AGNACNCCNG GRTANGTNGG YCC 23

( 2 ) INFORMATION FOR SEQ ID NO:16:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY:
        ( B ) LOCATION: 17
        ( D ) OTHER INFORMATION: /note= "Y = C or T"

( i x ) FEATURE:
        ( A ) NAME/KEY:
        ( B ) LOCATION: 20
        ( D ) OTHER INFORMATION: /note= "N = deoxyinosine"

( i x ) FEATURE:
        ( A ) NAME/KEY:
        ( B ) LOCATION: 23
        ( D ) OTHER INFORMATION: /note= "Y = C or T"

( i x ) FEATURE:
        ( A ) NAME/KEY:
        ( B ) LOCATION: 26
        ( D ) OTHER INFORMATION: /note= "Y = C or T"

( x i ) SEQUENCE DESCRIPTION: SEQ ID NO:16:

CTGAATTCCA TATGAAYCCN TYCAYGA 27

( 2 ) INFORMATION FOR SEQ ID NO:17:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY:
        ( B ) LOCATION: 3
        ( D ) OTHER INFORMATION: /note= "N = deoxyinosine"

( i x ) FEATURE:
        ( A ) NAME/KEY:
        ( B ) LOCATION: 6
        ( D ) OTHER INFORMATION: /note= "N = deoxyinosine"

( i x ) FEATURE:
  ( A ) NAME/KEY:
  ( B ) LOCATION: 9
  ( D ) OTHER INFORMATION: /note= "N = deoxyinosine"

( i x ) FEATURE:
  ( A ) NAME/KEY:
  ( B ) LOCATION: 12
  ( D ) OTHER INFORMATION: /note= "R = A or G"

( i x ) FEATURE:
  ( A ) NAME/KEY:
  ( B ) LOCATION: 15
  ( D ) OTHER INFORMATION: /note= "N = deoxyinosine"

( i x ) FEATURE:
  ( A ) NAME/KEY:
  ( B ) LOCATION: 18
  ( D ) OTHER INFORMATION: /note= "N = deoxyinosine"

( i x ) FEATURE:
  ( A ) NAME/KEY:
  ( B ) LOCATION: 21
  ( D ) OTHER INFORMATION: /note= "Y = C or T"

( x i ) SEQUENCE DESCRIPTION: SEQ ID NO:17:

AGNACNCCNG GRTANGTNGG YCC                       2 3

( 2 ) INFORMATION FOR SEQ ID NO:18:

( i ) SEQUENCE CHARACTERISTICS:
  ( A ) LENGTH: 24 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:18:

GGTACGATGA TGACGACCCG TTTG                      2 4

( 2 ) INFORMATION FOR SEQ ID NO:19:

( i ) SEQUENCE CHARACTERISTICS:
  ( A ) LENGTH: 23 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:19:

GGATGATTCC ATAGTCGACC GGG                       2 3

( 2 ) INFORMATION FOR SEQ ID NO:20:

( i ) SEQUENCE CHARACTERISTICS:
  ( A ) LENGTH: 21 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:20:

GTTGAGGGCT GGTCAAAACG C                        2 1

( 2 ) INFORMATION FOR SEQ ID NO:21:

( i ) SEQUENCE CHARACTERISTICS:
  ( A ) LENGTH: 21 base pairs
  ( B ) TYPE: nucleic acid ( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:21:

GCGTTTTGAC CAGCCCTCAA C 21

( 2 ) INFORMATION FOR SEQ ID NO:22:

( i ) SEQUENCE CHARACTERISTICS:
( A ) LENGTH: 24 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:22:

GAGATTGTGC ACTTCTTCCA GAGA 24

( 2 ) INFORMATION FOR SEQ ID NO:23:

( i ) SEQUENCE CHARACTERISTICS:
( A ) LENGTH: 24 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:23:

TCTCTGGAAG AAGTGCACAA TCTC 24

( 2 ) INFORMATION FOR SEQ ID NO:24:

( i ) SEQUENCE CHARACTERISTICS:
( A ) LENGTH: 26 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:24:

TGAATCCATT CCACGATTTA GAGCCT 26

( 2 ) INFORMATION FOR SEQ ID NO:25:

( i ) SEQUENCE CHARACTERISTICS:
( A ) LENGTH: 38 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:25:

GGGAATTCCA TATGAATCCA TTCCACGATT TAGAGCCT 38

( 2 ) INFORMATION FOR SEQ ID NO:26:

( i ) SEQUENCE CHARACTERISTICS:
( A ) LENGTH: 36 base pairs
( B ) TYPE: nucleic acid
( C ) STRANDEDNESS: unknown
( D ) TOPOLOGY: unknown ( i i ) MOLECULE TYPE: DNA (genomic)

(x i) SEQUENCE DESCRIPTION: SEQ ID NO:26:

CCGGAATTCA TGAATCCATT CCACGATTTA GAGCCT                                                          36

(2) INFORMATION FOR SEQ ID NO:27:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (i i) MOLECULE TYPE: DNA (genomic)

(x i) SEQUENCE DESCRIPTION: SEQ ID NO:27:

CGCGGATCCT CACTTCTTGA ATTTCTCCTT GTAAAG                                                          36

(2) INFORMATION FOR SEQ ID NO:28:

(i) SEQUENCE CHARACTERISTICS:
        (A) LENGTH: 250 base pairs
        (B) TYPE: nucleic acid
        (C) STRANDEDNESS: single
        (D) TOPOLOGY: unknown (i i) MOLECULE TYPE: DNA (genomic)

(x i) SEQUENCE DESCRIPTION: SEQ ID NO:28:

GAATTGTGAG CGCTCACAAT TCTAGGATGT TAATTGCGCC GACATCATAA CGGTTCTGGC        60

AAATATTCTG AAATGAGCTG TTGACAATTA ATCATCGGCT CGTATAATGT GTGGAATTGT        120

GAGCGGATAA CAATTTCACA CAGGAAACAG ACCATGGTGA ATTCTAGAGC TCGAGGATCC        180

GCGGTACCCG GGCATGCATT CGAAGCTTCC TTAAGCGGCC GTCGACCGAT GCCCTTGAGG        240

CCTTCAACCA                                                              250

What is claimed is:

1. A purified thermostable enzyme indegenous to *Thermococcus litoralis* which catalyzes the hydrolysis of inorganic pyrophosphate, wherein said enzyme has a molecular weight of 20–21 kDa when compared with protein standards including trypsin inhibitor (soybean) –21.5 kDa.

2. The thermostable enzyme of claim 1, wherein the enzyme is active after four hours incubation at 100° C. and has 100% of its activity at 72° C.

3. The thermostable enzyme of claim 1, wherein said enzyme is isolated from a recombinant organism transformed with a vector that codes for the expression of the enzyme.

4. An isolated DNA molecule which codes for the thermostable enzyme of claim 1.

5. The isolated DNA molecule of claim 4, wherein the DNA includes the nucleotide sequence (SEQ ID NO:9).

6. A cloning vector comprising the isolated DNA molecule of claim 4.

7. A host cell transformed by the vector of claim 6.

8. A method for producing a recombinant thermostable DNA inorganic pyrophosphatase from *Thermococcus litoralis* comprising culturing a host cell transformed with the vector of claim 6 under conditions suitable for transcribing and then translating the DNA molecule encoding the pyrophosphatase.

* * * * *

UNITED STATES PATENT AND TRADEMARK OFFICE
CERTIFICATE OF CORRECTION

PATENT NO. : 5,861,296
DATED : January 19, 1999
INVENTOR(S) : Tricia Lennox, et al It is certified that error appears in the above-identified patent and that said Letters Patent is hereby corrected as shown below:

In the Drawings:

| | |
|---|---|
| Sheet 4 of 18 | replace "Fig. 3B" with substitute --Fig. 3B-- |
| Sheet 13 of 18 | replace "Fig. 13A-1" with substitute --Fig. 13A-1-- |
| Sheet 14 of 18 | replace "Fig. 13A-2" with substitute --Fig. 13A-2-- |
| Column 4, line 38 | replace "solid black" with --with diagonal lines slanting upward left to right-- |
| Column 4, line 39 | replace "a lighter color" with --with diagonal lines slanting downward left to right-- |
| Column 12, line 12 | after "expression" insert --of-- |
| Column 9, line 18 | replace "Example", second occurrence, with --Examples-- |
| Column 10, line 5 | replace "1sBamH1o" with --1sBamHIo-- |
| Column 10, line 10 | replace "1sBamH1o" with --1sBamHIo-- |
| Column 13, line 15 | replace "maybe" with --may be-- |
| Column 13, line 26 | replace "Frtisch" with --Fritsch-- |
| Column 18, line 20 | after "approximately", first occurrence, please delete "870" |
| Column 18, line 21 | replace "1300" with --300-- |
| Column 20, line 39 | after "approximately", second occurrence, please delete "870" |
| Column 20, line 40 | replace "1300" with --300-- |
| Column 21, line 34 | replace "Teminator" with --Terminator-- |

UNITED STATES PATENT AND TRADEMARK OFFICE
CERTIFICATE OF CORRECTION

PATENT NO. : 5,861,296
DATED : January 19, 1999
INVENTOR(S) : Tricia Lennox, et al It is certified that error appears in the above-identified patent and that said Letters Patent is hereby corrected as shown below:

| | |
|---|---|
| Column 25, line 23 | replace "ß-lactoglublin" with --ß-lactoglobulin-- |
| Column 25, line 62 | replace "dephosphorolyated" with --dephosphorylated-- |
| Column 25, line 64 | replace "was" with --were-- |
| Column 29, line 33 | replace "hydrocholoride" with --hydrochloride-- |
| Column 31, line 46 | replace "example" with --Example-- |
| Column 32, line 22 | replace "example" with --Example-- |
| Column 32, line 31 | replace "sequence" with --sequenced-- |
| Column 32, line 39 | replace "disclosure" with --disclosures-- |

Signed and Sealed this

Twenty-fifth Day of April, 2000

Attest:

Q. TODD DICKINSON

*Attesting Officer*     *Director of Patents and Trademarks*

```
- D G K P V S A F - - - - - - - - - H D I P L Y A D K E
L N E R N F A A F T H R S A A A H P W H D L E I G P E A
            F E N K I V E A F - - - - - - - - - - - - - - - - -
                    S L L N V P A G K D L
                    M E S F - - - - - - - - - Y H S V P V G P K P
                    M N P F H D L E P G P E V

E E T L N P I I Q D T K K G K L R F V R N C F P H H G Y
N - - - - - - - - - - - - S G L I K V D R V L Y S S I V Y
E - - - - - - - - - - - - S G A L F V D R F M S T A M F Y
E - - - - - - - - - - - - R G I F K L D R V L Y S P M F Y
D - - - - - - - - - - - - F P G M L V D R V L Y S S V V Y
K - - - - - - - - - - - - T G L I K L D R V L Y S P F H Y

V - G D N D P I D V L E I G E T I A Y T G Q V K Q V K A
I C E D S D P M D V L V L M Q E P V L T G S F L R A R A
L S L D G D P V D V L V P T P Y P L Q P G S V I R C R P
L A L D G D P L D I L V I T T N P P F P G C V I D T R V
L Y Y D G D P M D V M V L I S Q P T F P G A I M K V R P
W Y D D D D P F D I M V I M R E P T Y P G V L I E A R P

P L A P K L N D I E D V E K Y F P G L L R A T N E W F R
- - - P E F R H Y R D I K E L P P H R L A E I R R F F E
- L S K E Y D H I K D V N D L P E L L K A Q I A H F F E
- - - P R F D E V R S I E D L P Q H K L K E I A H F F E
- - - P N V S Y I K D L K D V N A H L L D E I A N F F S

K Y A L D I I K E T H D S W K Q L I A G K S S D S
D A I K D S M D L Y E L T S K - - L A C N A N E E
A E I - - - V A S F E R A - K N K
K L I D E C I A R Y N - - - E Q K
K E I E V S I K M Y E E K Y G K K N

I P P A S L K A D A P I D K S I D K W F F I S G S V
F Y T T C M L D K I S I G - A F N F V M L I R K H C
```

FIG. 3B